United States Patent [19]
Castor et al.

[11] Patent Number: 5,877,005
[45] Date of Patent: Mar. 2, 1999

[54] VIRAL INACTIVATION METHOD USING NEAR CRITICAL, SUPERCRITICAL OR CRITICAL FLUIDS

[75] Inventors: Trevor P. Castor, Arlington, Mass.; Arthur D. Lander, Laguna Beach, Calif.; Maury David Cosman, Woburn, Mass.; Peter Richard D'Entremont, Walpole, Mass.; Michael Richard Pelletier, Stow, Mass.

[73] Assignee: Aphios Corporation, Woburn, Mass.

[21] Appl. No.: 547,851

[22] Filed: Oct. 25, 1995

Related U.S. Application Data

[63] Continuation-in-part of Ser. No. 844,513, Mar. 2, 1992.
[51] Int. Cl.⁶ .............................. A01N 1/02; C12N 7/06; C12M 3/02
[52] U.S. Cl. ............................ 435/238; 435/2; 435/286.1
[58] Field of Search .......................................... 435/238, 2

[56] References Cited

U.S. PATENT DOCUMENTS

| Re. 32,695 | 6/1988 | Nahra et al. | 261/118 |
|---|---|---|---|
| 4,749,522 | 6/1988 | Kamarei | 260/412.8 |
| 5,520,943 | 5/1996 | Osajima et al. | 426/422 |
| 5,667,835 | 9/1997 | Osajima et al. | 426/521 |

*Primary Examiner*—Sandra E. Saucier

[57] ABSTRACT

The invention involves the use of supercritical or near-critical fluids for the inactivation of viruses, especially enveloped or lipid protected viruses, and nonenveloped, protein encased viruses, viral-like particles and other pathogens in any matrix, but preferably in solutions containing biologically active proteinaceous products of natural or genetic engineering origin or in semi-solid or solid support matrices which are thermally labile or sensitive to conventional viral inactivation techniques. Novel apparatus also are provided.

12 Claims, 7 Drawing Sheets

5,877,005

VIRAL INACTIVATION METHOD USING NEAR CRITICAL, SUPERCRITICAL OR CRITICAL FLUIDS

This application is a continuation-in-part of U.S. Ser. No. 07/844,513, filed Mar. 2, 1992, entitled "Viral Inactivation Method and Apparatus".

FIELD OF INVENTION

This invention relates to methods and apparatus for the inactivation of viruses using critical, near critical and/or supercritical fluids.

BACKGROUND OF THE INVENTION

Infectious viruses, unless inactivated, can be readily transmitted from biological products derived from human plasma as well as recombinant-DNA and monoclonal antibody sources. The hepatitis B virus (HBV) as well as the agents of non-A and non-B hepatitis (NANBHV) have plagued patients, physicians and manufacturers for many years. In recent years, the human immunodeficiency virus (HIV)—the etiologic agent of acquired immunodeficiency syndrome (AIDS)—has become a very serious and epidemic problem. In several instances, coagulation factor concentrates have transmitted HIV to hemophiliacs, some of whom have subsequently developed AIDS (an estimated 65% of the 20,000 hemophiliacs in the United States are infected with HIV, Wall Street Journal, Dec. 27, 1990. Morgenthaler, a leading researcher in this field, states in his preface to *Viral Inactivation in Plasma Products* (1989) that: "Clearly, there is a need for methods that inactivate viruses in blood, without causing harm to the components intended for therapeutic use."

Viral inactivation of recombinant-DNA products is still a major and active concern for the biotechnology and pharmaceutical industries as well as the regulatory agencies. The FDA in *Points to Consider in the Manufacture and Testing of Monoclonal Antibody Products for Human Use* states that: "It is strongly recommended that validated procedures . . . which remove and/or inactivate viruses and DNA if present be employed during purification. . . ." For reasons of safety and public health, the quest is to discover and develop processes for inactivating viruses without denaturing the biologically active products which are commonly labile and quite sensitive to conventional viral inactivation techniques.

There exists substantial difficulty in inactivating viruses in the presence of thermally labile and sensitive proteins without utilizing additives which may be carcinogenic, toxic and/or damaging to biologically active compounds. These additives, which must be removed in a sterile post-process step, place an additional cost and time burden on conventional viral inactivation techniques.

Embodiments of this invention provide novel methods and apparatus for inactivating viruses, especially enveloped or lipid-coated viruses, and nonenveloped, protein encased viruses in proteinaceous products without incurring substantial denaturation.

SUMMARY OF INVENTION

The present invention is directed to methods and apparatus for inactivating virus and virus-like particles. One embodiment of the present invention comprises a method of inactivating one or more virions associated with a material. The method comprises the steps of contacting a material with a critical, near critical or supercritical fluid. The critical, near critical or supercritical fluid is capable of being received by at least one virion and upon removal, causes inactivation of the virion. The method further comprises the step of removing the critical, supercritical or near critical fluid from the material and one or more virions to render one or more virions inactive.

As used herein, the term "virus" is used to include viruses and virus-like particles. A "virion" is an individual virus entity or particle. As used herein, the term "inactive" means the virion particle is unable to replicate or infect a host cell.

In the field of physical chemistry, the term "critical fluid" refers to a gas at or above its critical temperature and at or above its critical pressure. The term "supercritical fluid" refers to a gas above its critical temperature and above its critical pressure. Supercritical fluids are sometimes designated in this application by the abbreviation "SCF." The term "near critical" is used in the sense of approaching or close to being critical. At or near the critical pressure and temperature, SCoCoNC fluids conform to the equation:

$$Tr=To/Tc$$

where Tr is the reduced temperature in absolute degrees; To is the absolute operating temperature; and Tc is the absolute critical temperature. A preferred range of Tr is 0.1 to 2.0.

At or near the critical pressure and temperature SCoCoNC fluids conform to the equation:

$$Pr=Po/Pc$$

where Pr is the reduced pressure; Po is the operating pressure; and Pc is the critical pressure. A preferred Pr is 0.2 to 20.0, and most preferably 0.5 to 10.0. As used herein, the term "near critical" means having a reduced pressure, Pr of 0.2–1.0 and/or reduced temperature, Tr, of 0.10–1.0.

One example, without limitation, of a near critical fluid is a gas having a temperature below its critical temperature and a pressure at or above the critical pressure. Such gas has properties which, may approach those of a supercritical or critical fluid, particularly in solvating properties.

In industrial settings where critical, supercritical and near critical fluids are used, it is common, particularly where the solvent properties are being applied, to use the term "critical" to refer to supercritical, critical and near critical fluids. This application will use the term "SCoCoNC fluid" to represent supercritical, critical or near critical fluids. Fluids are sometimes referred to in the examples as "critical" as a convenience, even though such fluids may be supercritical, critical or near critical.

SCoCoNC fluids exhibit solvent powers related to the solvent density at a particular temperature and pressure. Solvating properties of SCoCoNC fluids are influenced by cosolvents and entrainers. The terms "cosolvents" and "entrainers" are used interchangeably to suggest compositions which are soluble in the SCoCoNC and impart desirable solubility features to the SCoCoNC to which they are added with respect to phospholipids and aqueous phases. Nonpolar cosolvents refer to compositions having no or slight dipole moment, ranging approximately from 0.0 to 0.1 Debyes. Polar cosolvents refer to compositions having a dipole moment, ranging approximately from 0.1 to 1.7 Debyes.

Preferably, the SCoCoNC fluid is selected from the group of compositions capable of forming critical fluids comprising binary gases carbon dioxide; nitrous oxide; halohydrocarbons, such as freon; alkanes such as propane and ethane; and alkenes, such as ethylene.

As used herein, the term "contacting" means exposing to and coming together. The term "receiving" means taking in, in a manner to have an effect.

The material to be treated may be a solid or fluid. For example, the present invention is well suited for inactivating one or more virions associated with medical appliances, tools or devices. The present method is ideally suited for biological materials. SCoCoNC fluids inactivate viruses under conditions which preserve the biological activity of many useful proteins and peptides.

A preferred biological material has an aqueous phase. As used herein, the term "aqueous phase" refers to a composition comprising in whole, or in part, water.

Biological materials having a liquid component are capable of forming an admixture with the SCoCoNC fluid. Preferably, the admixture is formed under laminar flow conditions. A Reynolds Number is a ratio of inertia to viscous forces. The number is a measure of turbulence. Numbers having values greater than 2,000 suggest turbulent conditions.

Preferably, ScoCoNC fluids are diffused into laminar, small-diameter aqueous droplets or streams. Preferably, the droplets or streams have a Reynolds Number, which value is maintained lower than turbulent values. That is, an admixture of the biological materials and SCoCoNC fluid is formed under mixing conditions with a Reynolds Number less than or equal to 2,000.

Surprisingly and unexpectedly, whereas turbulent mixing may require thirty minutes to two hours to effect a $10–10^6$-fold reduction in active virus, non-turbulent mixing may effect a 100-fold reduction in active virus in twenty seconds.

Non-turbulent mixing, to form an admixture of the biological material and the SCoCoNC fluid, further minimizes shear forces, reducing possible protein damage. Contact with the walls of the containment vessel is minimized, reducing possible protein loss.

Embodiments of the present method are ideally suited for biological materials which are used therapeutically. Ideally these materials must be substantially virus free. In a practical sense, one reduced the viral load of such material to acceptable detection limits for viral pathogens. Embodiments of the present invention are useful in reducing viruses associated with material. Viruses of primary interest at this time, blood products are parvovirus, HBV, HAV, NANBHV, and HIV.

The biological materials may comprise proteins, peptides, nucleic acids, biologically active small molecules, platelets, and blood factors. These biological materials may be further isolated; however, embodiments of the present method are not in themselves directed to isolating such materials. Rather, embodiments of the present invention are capable of inactivating virus associated with a sample without a substantial loss of the biological material, allows such materials to be further processed if desired.

A further embodiment of the invention features apparatus for inactivating one or more virion associated with a sample. The apparatus comprises means for containing a sample and SCoCoNC fluid. The SCoCoNC fluid is received by one or more virions associated with the sample. The apparatus further comprises means for removing the SCoCoNC fluid and upon removal of the SCoCoNC fluid, one or more virions associated with the samples is inactivated.

Means for containing the sample and SCoCoNC fluid may take several forms. For surgical equipment, such means may comprise a vessel adapted to receive the equipment and a SCoCoNC fluid. For fluid samples, such means may comprise soaking chambers and mixing chambers.

A preferred mixing chamber diffuses the SCoCoNC fluid into laminar, small diameter aqueous droplets or streams of the sample. Preferably, the flow of sample into the mixing chamber is at a rate to obtain a low Reynolds Number, of less than or equal to 2,000. That is, the rate of flow of the sample is nonturbulent. Contact with the SCoCoNC fluid may be for as short a period of time as twenty seconds, to achieve a $10–10^6$-fold reduction in viral load. The sample can be reintroduced to the SCoCoNC in additional cycles or stages to achieve a desired viral load.

Embodiments of the present invention allow for a reduction in the viral load of a sample. Embodiments of the present invention are capable of reducing viral load without substantial damage to proteins, and other desirable biological materials. The methods and apparatus of the present invention are readily scalable.

These and other features and advantages are described more fully in the Figures, description and Examples which follow.

BRIEF DESCRIPTION OF THE DRAWINGS

FIG. 4a illustrates a droplet of sample within such apparatus;

DETAILED DESCRIPTION

The present invention will be described in detail as a method and apparatus for inactivating one or more virions associated with a material. The inactivation of one or more virions is reflected in a reduction in the viral load associated with the material. The methods and apparatus of the present invention feature SCoCoNC fluids.

Figure 1:
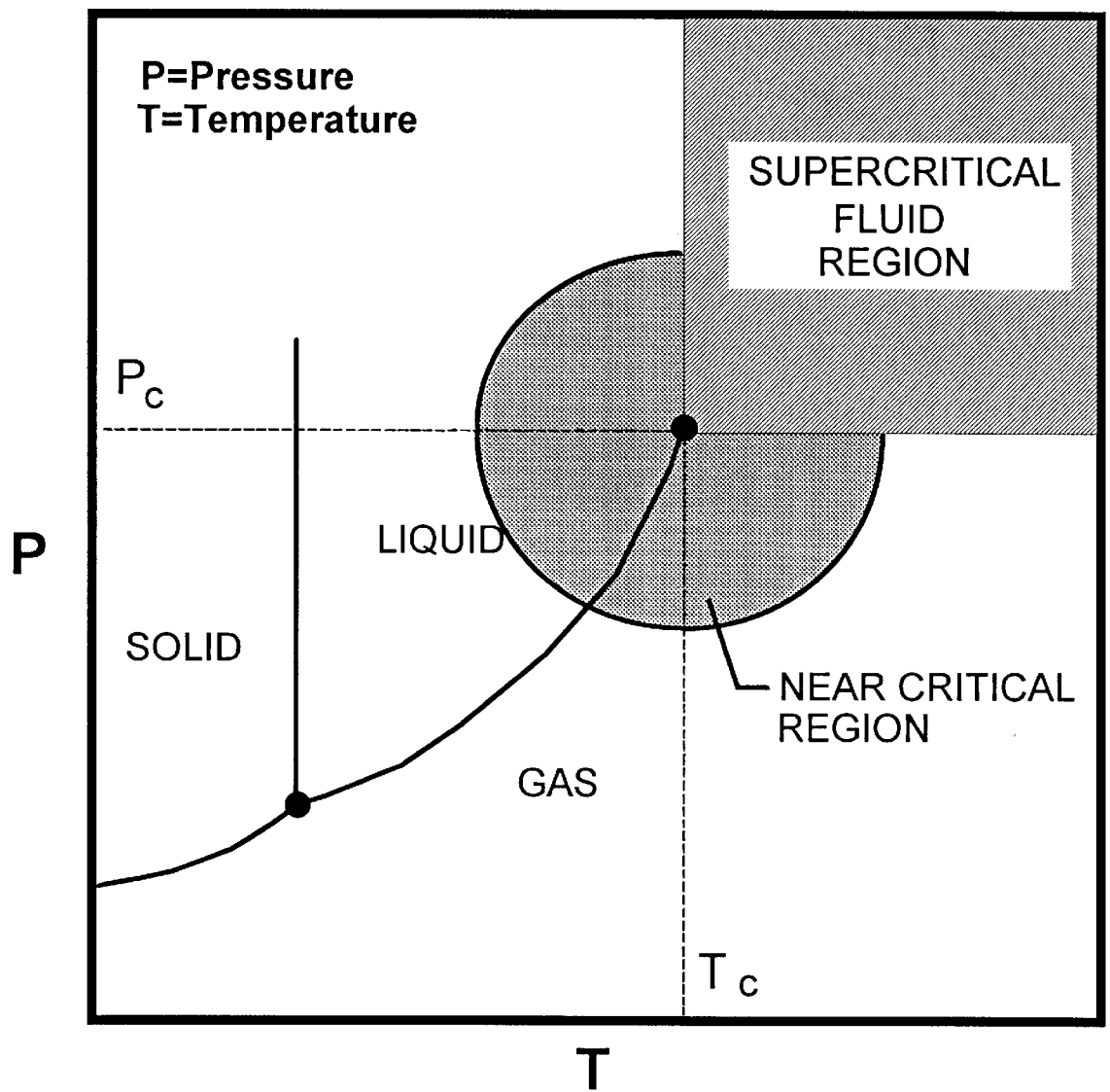
FIG. 1 is a graphical description of the physical states of a fluid under the influence of pressure and temperature.

FIG. 1 illustrates graphically a pure component compound at different pressures and temperatures. SCoCoNC fluids are gases at ambient temperature and pressure. As a function of pressure and temperature, these gases take on special intrinsic properties. As an intrinsic thermodynamic property, these gases become dense phase fluids at a particular pressure and temperature. These dense phase fluids, critical fluids, exhibit liquid-like density and gas-like properties of diffusivity and viscosity.

The near critical region or FIG. 1 defines near critical fluids. In this region, the fluids exhibit similar solvating properties as the fluid under critical or supercritical conditions.

Preferred fluids are those that are gases at ambient conditions and that have critical temperatures of between 0° C. and 100° C., most preferably between 0° C. and 60° C. When working with biological material (e.g. proteinaceous material), fluids with critical temperatures of substantially less than 60° C. (e.g. 40° C.) are preferred so as to further preserve biological activity. As a practical matter, a temperature of above 0° C. is desired with aqueous systems to avoid freezing the sample.

Preferred fluids includes fluorocarbons such as chlorodifluoromethane, alkanes such as ethylene, propane and ethane, and binary fluids such as nitrous oxide and carbon dioxide. These fluids can be used with small quantities of polar entrainers or modifiers, known in the art as cosolvents. Cosolvents include substances such as ethanol, methanol, acetone, and ethylene glycol. Such cosolvents can effect inter alia the polarity of the critical fluid, thereby enhancing the capacity of the critical fluid to inactivate virus in certain materials.

The materials to be treated may be any material that can be brought in contact with a selected SCoCoNC fluid. The present method and apparatus can be used to reduce the viral load of medical equipment, membranes, devices and the like.

Embodiments of the present method and apparatus are ideally suited for inactivating one or more virions associated with biological materials. The SCoCoNC fluid is selected to have minimal effects on the material in its arena of intended use. The invention is particularly applicable to proteinaceous materials attached to a solid support matrix or contained in a solution. Examples include blood plasma, blood plasma fractions, serum used for mammalian cell culture and solutions containing recombinant-DNA derived proteins. The protein may be contained in living cells, although typically the material treated is noncellular. The process also has applicability to the inactivation of viruses and other particle-like pathogens in semi-solid and solid matrices which are labile such as foods, spices, pharmaceutical powders and tablets.

A particular SCoCoNC fluid will be selected based upon at least two factors. The fluid selected should be capable of inactivating virus to the desired degree. Secondly, the fluid should be selected to minimize the affect on the material being treated. In the case of a protein, a fluid having an operating temperature below 60° C. and that does not tend to chemically denature the protein or otherwise adversely interact with the protein is preferred.

The particular fluid selected as well as the time of exposure of the critical fluid to the material, the temperature of the mixture and the pressure of the mixture are interdependent and together or individually may determine the appropriate conditions for the desired result. The time of exposure of the material to the critical fluid may affect the degree of viral inactivation. Thus, conditions for treating the material include those of sufficient time exposure to ensure that the material after treatment has the desired reduction in virus.

The time of exposure as well as the temperature together may affect the biological activity of a treated, isolated material. In connection with proteins, it is preferred to select conditions such that the desired biological activity of the protein is retained to a greater degree than virus. That is, the process reduces viral load at a rate which exceeds the loss of biological activity. By substantially retained it is meant that at least 50° C. of the desired biological activity is retained.

Preferably, the material is separated from the critical fluid under aseptic conditions. In the case of a solution containing, for example, a protein, to accomplish separation, the mixture is decompressed thereby resulting in a phase separation of the fluid from the solution containing the proteinaceous product. The material then is isolated under aseptic conditions.

By isolating the material it is meant separating the material from the equipment of the invention such as in a sterile bottle or a container (e.g. a flask) or in a package such as a hermetically sealed package. It does not include simply separating the material from the critical fluid into a compartment or container that is part of the sterilization equipment of the invention. It should be understood, nevertheless, that the containers or packages used in isolating the material may be at least temporarily attachable to the equipment of the invention so as to facilitate transfer of the material from the equipment to its isolated state in a sterile container or package. The treated material also may be first collected from the equipment and then filtered such as through a filter to remove bacteria in order to isolate the material under aseptic conditions.

Figure 2:
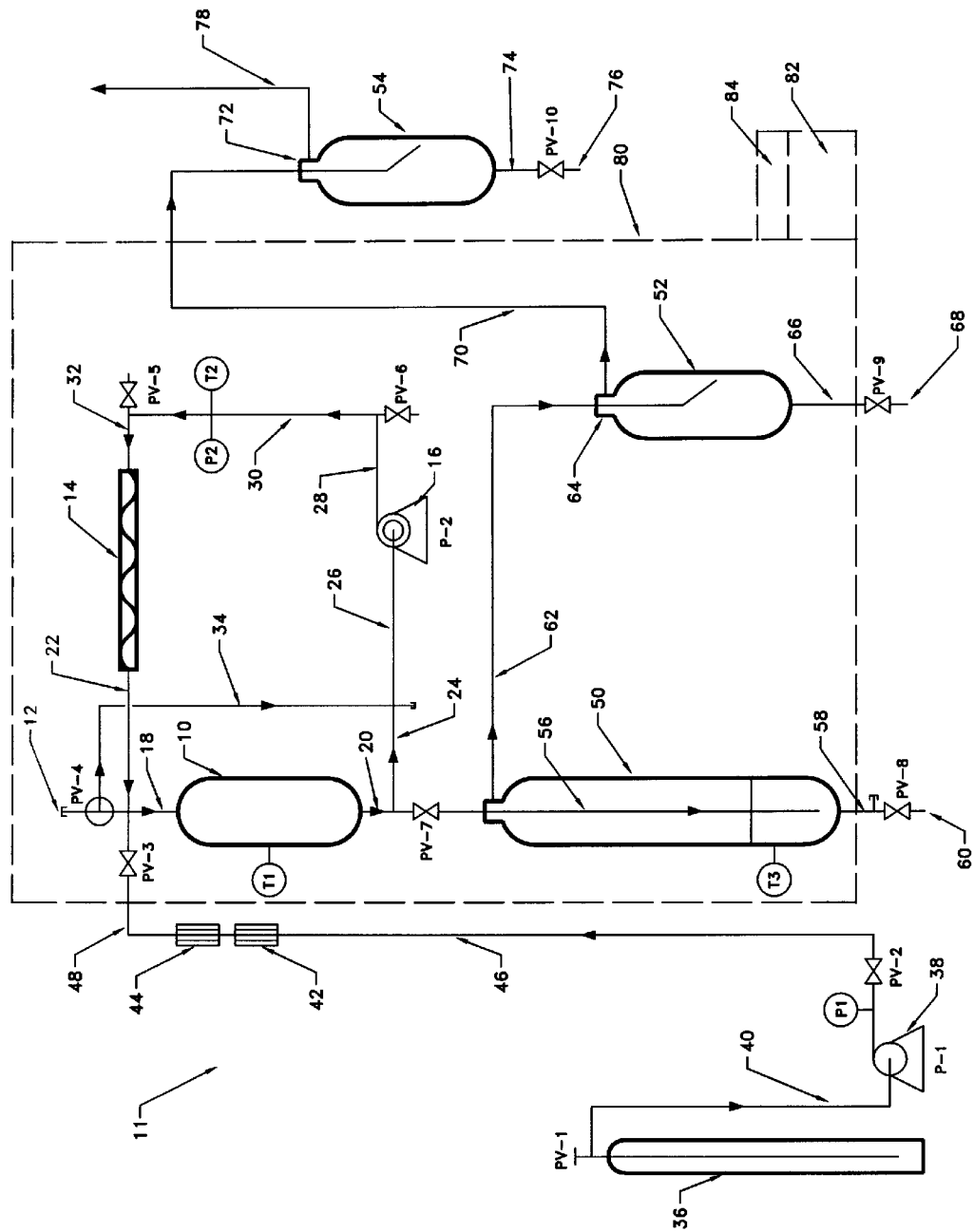
FIG. 2 is a schematic illustration of an apparatus embodying features of the present invention.

Turning now to FIG. 2, a preferred apparatus, generally designated by the numeral 11, for inactivating one or more virions, is illustrated. The apparatus includes a source of fluid, a high-pressure, recirculation loop, a separation chamber, and at least one low pressure trap. Viral inactivation occurs in the high-pressure recirculation loop, which is rated for continuous operation at 5,000 psig and 100° C.

The high-pressure recirculation loop consists of: a chamber 10 into which the material to be treated and the critical fluid are introduced; an injection port 12 for introducing the product into the soaking chamber; a static in-line mixer 14 for continuously mixing the mixture of product and fluid; and a circulation pump 16 for moving the mixture to the in-line mixer 14; two thermocouples, one associated with the separation chamber (thermocouple T1) and the other located just upstream of the in-line mixer (thermocouple T2); a pressure indicator P2 also located just upstream of the static in-line mixer; and various interconnecting lines 18, 20, 22, 24, 26, 28, 30, 32, 34 and 36 as well as several process valves PV-3, PV-4, PV-5, PV-6 and PV-7 for channeling and controlling the movement of fluid throughout the high-pressure recirculation loop.

Process valves PV-3, PV-5, PV-6 and PV-7 are all ¼" full-opening two-way Stainless Steel ball valves rated for 6,000 psig at 100 C. (Parker, Huntsville, Ala.); PV-4 is a three-way stainless steel ball valve (Parker, Huntsville, Ala.). In some embodiments of the invention, process valve PV-7 is a back-pressure regulator (Model No. 26-1722-24, Tescom Corporation, Elk River, Minn.) with which the operator can control the decompression of the separation chamber and the high pressure circulation loop. The particular soaking chamber 10 employed was a high pressure stainless steel vessel having a capacity of 150 ml and an operating pressure of 5,000 psig at 100 C. (Model Z148, Hoke Inc., Cresskill, N.J.). A K-type thermocouple T1 was placed in contact with the outer surface of the soaking chamber 10 and the temperature monitored on a digital temperature-indicator-controller (Model No. CN-310KC, Omega Engineering, Inc., Stamford, Conn.).

The soaking chamber 10 has a top inlet line 18 and a bottom outlet line 20. The inlet line 18 communicates at a fluid joint with the source of critical fluid, the product injection port 12, and the outlet line 22 of the static in-line mixer 14. The outlet line 20 of the soaking chamber 10 and one end of conduit line 24 are connected at a fluid joint which joint in turn is connected to the decompression valve PV-7. The other end of conduit line 24 is connected at a fluid joint to the inlet line 26 of the circulation pump 16. The particular circulation pump 16 used was a variable speed (0 to 9,000 rpm), high pressure (5,000 psig at 150 C.) gear pump capable of a flow rate of 300 ml/min at a pressure differential of 10 to 20 psig (Modified Model No. 183, custom-built by Micropump, Concord, Calif.). The circulation pump 16 had a cooling head made of an aluminum block connected to a circulating, refrigerated water bath capable of maintaining temperatures as low as 5° C. and a cooling rate 15,300 Btu/h (Model No. HX-150, Neslab, Inc., Concord, N.H.). The discharge line 28 of circulation pump 16 is connected at a fluid joint to one end of the conduit line 30, which joint in turn is connected to drain valve PV-6. The other end of conduit line 30 is connected at a fluid joint to the inlet line 32 of the static in-line mixer 14 which joint in turn is connected to vent valve PV-5. Conduit 30 has an in-line pressure indicator P-2 and an in-line K-type thermocouple T2 which is connected to a temperature-indicator controller (Model No. CN-310KC, Omega, Stamford, Conn.).

The particular static in-line mixer 14 employed was a ³⁄₁₆" ID×7½" long×27 element tube mixer rated for 4,642 psig at 300 F. (Kenics Mixer Model No. 37-03-075, Chemineer, Dayton, Ohio). The outlet line 22 of the static in-line mixer 14 and the inlet line 18 to the separation chamber 10 are connected at a fluid joint. This joint is connected to critical fluid feed valve PV-3 and also is connected to the three-way process valve PV-4. The three-way process valve PV-4 allows fluid connection between the injection port 12 and either the recycle conduit 34 or the inlet line 18 of the soaking chamber 10. The recycle conduit at its other end is connected to the joint between the conduit line 24 and inlet 26 of the circulation pump 16.

The critical fluid is in fluid communication with feed valve PV-3 via a series of conduit lines interrupted by valves, pumps and filters. Release of critical fluid from the container 36 is controlled by valve PV-1 on the head of the high pressure container. The fluid is conducted from the container 36 to the inlet of compressor 38 via conduit line 40. The particular compressor employed was a single-ended diaphragm compressor which can compress gas or liquid up to 10,000 psig at a flow rate of 40 standard liters per minute (Model No. J-46-13411, Superpressure Gas Compressor, Newport Scientific, Jessup, Md.). A process valve PV-2 is connected to the outlet of the compressor 38 and can be closed when the desired pressure is achieved. The fluid is conducted from the compressor 38 to a pair of in-line filters 42, 44 via conduit line 46. The particular in-line filters used were a 7 micron sintered stainless steel cup filter 42 (Model No. SS-8F-K4-7 in a 6TF stainless steel housing, Nupro Company, Willoughby, Ohio) and a 0.5 micron sintered stainless steel cup filter 44 (Model No. SS-8F-K4-05 in a 6TF stainless steel housing, Nupro Company, Willoughby, Ohio). The fluid exits the outlet of filter 44 and is conducted via conduit 48 to valve PV-3.

The high pressure recirculation loop interfaces with the product recovery, low pressure half of the apparatus which is made up of a 500 ml decompression chamber 50, a first low pressure trap 52, and several two-way valves and connecting lines. The exhaust system consists of a second low pressure trap 54 leading to a vent line which exhausts to the atmosphere. In other embodiments of this invention, the vented critical fluid is first filtered and then recycled to the inlet of the compressor P-1.

The mixture in the soaking chamber 10 can be moved through the outlet line 20 via decompression valve PV-7 to a decompression tube 56 which extends to within about ¼" of the bottom of decompression chamber 50. The decompression chamber 50 has one inlet through which decompression tube 56 is inserted and sealed, and two outlet lines. The bottom outlet line 58 exits the bottom of the chamber 50 and is connected to process valve PV-8 (same type as PV-2) which in turn is connected to a sample port 60 for the recovery of liquid solvents and slurries. The top outlet line 62 exits the top of the decompression chamber 50 and is connected to low pressure trap 52. The particular decompression chamber employed was a 500 ml stainless steel high pressure chamber rated for 5,000 psig at 100 C. (Model No. Z152, Hoke Inc., Cresskill, N.J.).

The low pressure trap 52 has one inlet 64 through which the top outlet line 62 of the decompression chamber 50 is inserted and sealed. It also has two outlet lines. The bottom outlet line 66 exits the bottom of the low pressure trap 52 and is connected to process valve PV-9 which in turn is connected to a sample port 68 for the recovery of any liquid solvents and slurries carried over during the decompression process. The top outlet line 70 exits the top of low pressure trap 52 and is connected to a second low pressure trap 54. The second low pressure trap 54 has one inlet 72 through which the top outlet line 70 of low pressure trap 52 is inserted and sealed and two outlet lines. The bottom outlet line 74 exits the bottom of the second low pressure trap 54 and is connected to process valve PV-10 which is connected to a sample port 76 for the recovery of any liquid solvents and slurries carried over during the decompression process. The top outlet line 78 exits the top of second low pressure trap 54 and is vented to atmosphere. The particular low pressure traps employed were 150 ml high pressure Monel chambers rated for 5,000 psig at 100 C. (Model No. Z152, Hoke Inc., Cresskill, N.J.).

For reasons of safety and equipment flexibility, the product recovery half of the apparatus was also designed for continuous operation at a pressure of 5,000 psig at 100 C. Both the high pressure circulation loop and the product recovery half of the apparatus are enclosed in a polycarbonate (Lexan) box 80 which serves as a containment chamber. This chamber is heated by a 1500 W (Pelonis) heater 82 and controlled by a solid state ON-OFF temperature-indicator-controller 84 (Model No. CN-310KC, Omega, Stamford, Conn.) based on the in-line temperature T2 in conduit 30 attached to the discharge line 28 of the circulation pump P-2 16.

As an initial condition, the system is cleaned, sterilized and dried, and is at operating temperature (room temperature to 40 C.) with all process valves (PV) in the closed position.

To accomplish this, the system was rinsed with 0.5 mM EDTA in order to complex and remove any metal traces on the inside of the apparatus. The system was sterilized by filling with 70% ethanol solution via the 7 micron and the 0.5 micron filter elements. The system was then heated to 40 C. and the ethanol circulated in the high pressure circulation loop of the apparatus for about 30 minutes. The blowdown valve PV-7 was then opened and the entire system filled with 70% ethanol to the vent valve after LPT-2. All valves, namely PV-4, PV-5, PV-6, PV-8, PV-9 and PV-10, were bled until ethanol was seen. Valves PV-4 and PV-6 were covered with gauze soaked in 70% ethanol and then covered with aluminum foil. The system was held at 40 C. for approximately 30 minutes. The ethanol was then displaced from the system with pressurized (around 100 psig) and filtered (through the 7 micron and 0.5 micron filters) nitrogen through valves PV-6, PV-8, PV-9 and PV-10. When liquid was no longer coming out, these valves were all covered with ethanol soaked gauze and aluminum foil. The entire system was then rinsed with 0.2 micron filtered distilled and deionized (DDI) water. All valves were bled and the water displaced out of the system using filtered nitrogen under pressure. The sample loading tube, collection flasks and the fill bell (with silicon tubing attached) were all sterilized in an autoclave set at 250 F. for 30 minutes on fast exhaust. The loading tube was wrapped in gauze; about 2 ml of DDI water (in order to generate steam) was placed in the flasks which had a gauze and cotton plug covered with aluminum foil. When the steam cycle was completed, a 20 minute drying cycle was conducted.

In its normal operating mode, valves PV-4 and PV-5 are opened and an aliquot of test solution is aseptically introduced through the 3-way valve PV-4 using a sterile syringe and a presterilized loading tube. The 3-way valve PV-4 is then turned so that the critical fluid recycle line communicates with the soaking chamber, and the vent valve PV-5 is closed. PV-1 is then opened, supplying the solvent to the compressor P-1. The compressor is turned on and immediately thereafter valves PV-2 and PV-3 are opened, introducing the critical fluid solvent into the high pressure circulation loop. When operating pressure is attained, the compressor is turned off and valve PV-3 is closed.

After system stabilization, the circulation pump P-2 is turned on and its speed adjusted, typically to 75% of maximum speed or 6,750 rpm. P-2 draws both the proteinaceous product from the bottom of the soaking chamber and the critical fluid phase from the top of the same unit. The mixture is then pumped counter-clockwise, mixed by static in-line mixer and returned to the soaking chamber. After mixing for a defined residence time, P-2 is turned off. The decompression valve PV-7 is then fully opened to depressurize the soaking chamber and the high pressure circulation loop. The rate of decompression was approximately 500 psi per second when PV-7 is a ¼" ball valve. By using a back-pressure regulator instead of a ¼" ball valve as the decompression valve PV-7, the rate of decompression can be controlled. In some experiments, the rate of decompression was controlled to approximately 1,000 psi per minute. No differences were observed between rapid (500 psi per second) and slow (1,000 psi per minute) rates of decompression on the impact of critical fluid on viral infectivity and product activity. The experiments in Example 1 below were conducted with slow decompression while the experiments in the remaining examples presented below were conducted with rapid decompression. After decompression, product was aseptically collected into a sterile flask from the decompression chamber 50 through sample port 60 which was aseptically connected to a sterile fill bell. The collected sample was stored on ice until assayed.

Figure 3:
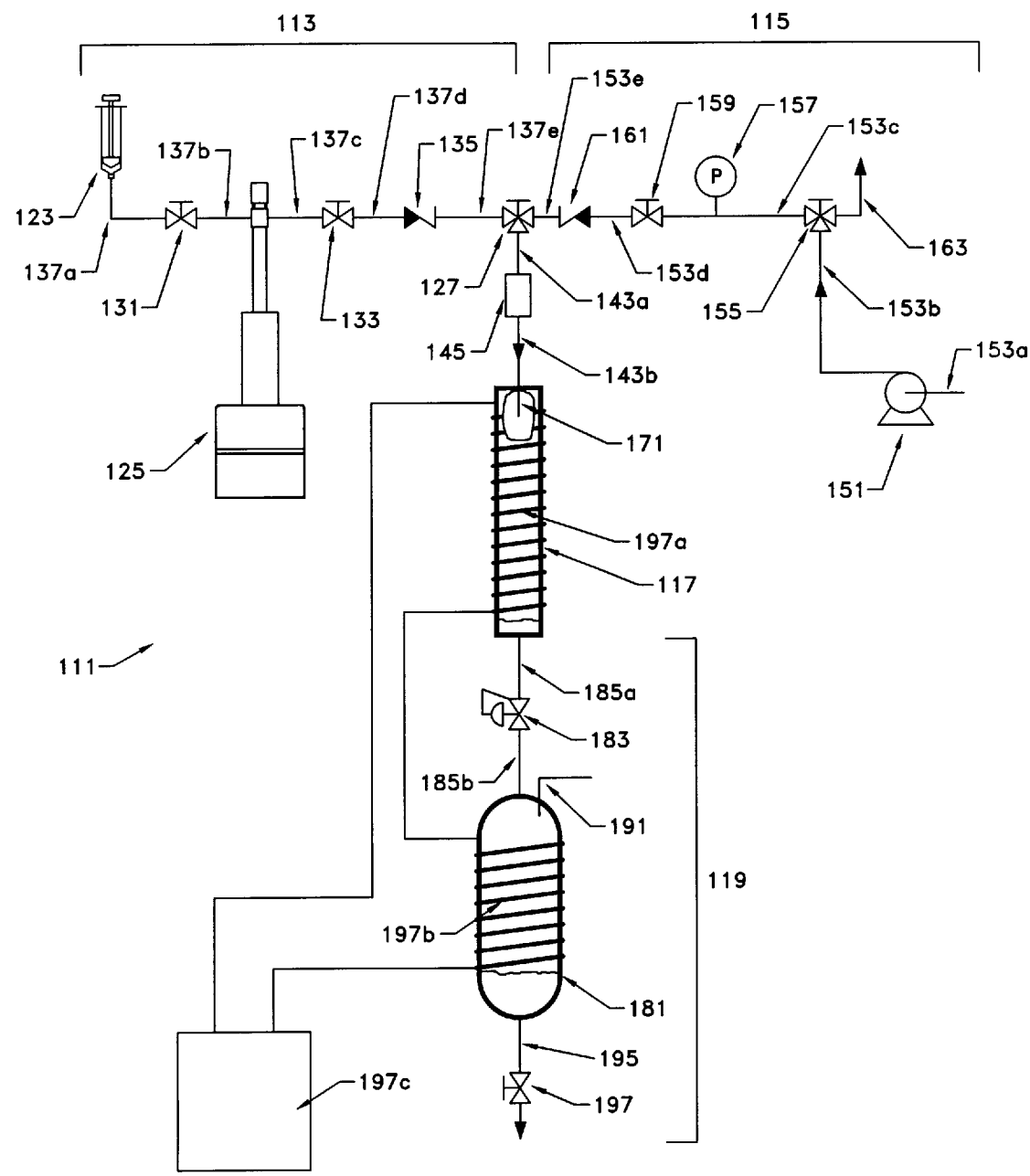
FIG. 3 is a schematic illustration of an apparatus embodying features of the present invention.

A further embodiment of the present invention is illustrated in FIG. 3. An apparatus, generally designated by the numeral 111, is depicted. An apparatus 111 is comprised of the following major components, sample injection assembly 113, SCoCoNC injection assembly 115, laminar mixing vessel 117, and sample withdrawal assembly 119.

Sample injection assembly 113 receives sample and directs sample into laminar mixing vessel 117. Sample injection assembly 113 comprises sample injection port 123, pump 125, three way valve 127, valves 131 and 133, one-way valve 135 and conduit 137. Sample injection port 123 is in fluid communication with valve 131 via conduit 137a.

Valve 131 is in fluid communication with pump 125 via conduit 137b. Pump 125 is capable of receiving sample from the sample injection port 123 through valve 131. A preferred laboratory scale pump is an Isco Pump 100 DM. Pump 125 is in fluid communication with valve 133 and one-way valve 135 via conduit 137c and conduit 137d, respectively. One way valve 135 prevents back flow of sample and ScoCoNC fluid into the sample injection assembly 13.

One way valve 135 is in fluid communication with three way valve 127 via conduit 137e. Three way valve 127 is capable of receiving sample and directing sample through conduit 143a, filter 145, and conduit 143b into laminar mixing vessel 117.

ScoCoNC fluid injection assembly 115 receives a ScoCoNC fluid from a source [not shown] and directs such fluid to the laminar mixing vessel 117. ScoCoNC fluid injection assembly 115 is comprised of pump 151, conduit 153, three way valve 155, pressure meter 157, valve 159 and one way valve 161. Pump 151 receives SCoCoNC fluid from a source [not shown] via conduit 153a. A preferred pump 151, for laboratory scale, is a Haskel pump. Pump 151 is in fluid communication with three way valve 155 via conduit 153b. Three way valve 155 is capable of releasing SCoCoNC via vent 163 or directly SCoCoNC fluid to valve 159 via conduit 153c. Pressure meter 157 is in communication with conduit 153c to provide pressure readings.

Valve 159 is in fluid communication with one way valve 151 via conduit 153d. One way valve 161 prevents the back flow of sample and SCoCoNC in SCoCoNC injection assembly 115.

One way valve 161 is in fluid communication with three way valve 127. Three way valve 127 is in communication with laminar mixing vessel 117 via conduit 143, filter 145 and conduit 143b.

Figure 4:
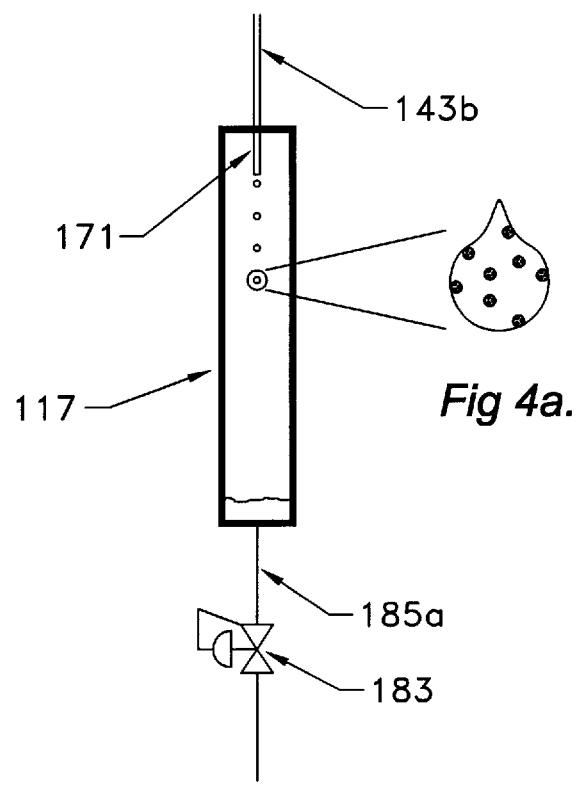
FIG. 4 is a schematic illustration of an apparatus embodying features of the present invention.

Turning now briefly to FIG. 4, laminar mixing vessel 117 comprises a closed container in fluid communication with sample injection assembly 113 and SCoCoNC fluid injection assembly 15 via conduit 143b. A nozzle 171 extends into the vessel for injecting sample at a controlled rate. Preferably the rate of injection is nonturbulent. For laboratory scale equipment, a 0.005 internal diameter tube is preferred. A nozzle 171, shown in cut away, of such dimensions is capable of nonturbulent injection of fluid sample up to 10 ml/minute. The sample is injected as a droplet or stream as illustrated in FIG. 4. A fine droplet, as illustrated in FIG. 4a, or stream allows SCoCoNC fluid to readily enter the liquid and virus within the droplet. Virus is depicted as darkened circles in the droplet in FIG. 49. The droplets or stream preferably have a flow having a Reynolds Number≦2,000.

Returning now to FIG. 3, the sample and SCoCoNC fluid forms a mixture contained in the bottom of laminar mixing vessel 117. Laminar mixing vessel 117 is in fluid communication with sample withdrawal assembly 119.

Sample withdrawal assembly 119 comprises defoaming chamber 181, back pressure regulator 183, and conduit 185. Defoaming chamber is in fluid communication with laminar mixing vessel 117 via conduit 185a and b and back pressure regulator 183. Conduit 185a receives samples and SCoCoNC fluid mixtures from the bottom of laminar mixing vessel 117. Back pressure regulator 183 is preferably adjusted to release fluid to defoaming chamber 181 in coordination with the flow of sample into laminar mixing vessel 117.

SCoCoNC fluid is released from the sample and SCoCoNC mixture in defoaming chamber 181. SCoCoNC fluid is removed from defoaming chamber 181 via conduit 191. Conduit 191 is preferably in communication with a flow meter [not shown] and a bleach trap to capture and kill any microorganisms surviving the process. The SCoCoNC is vented or recycled.

Sample without SCoCoNC fluids collects in defoaming vessel 181 and is removed via a port conduit 195 and valve 197.

The sample can be reintroduced into laminar mixing vessel 171 to obtain further cycles of contact with SCoCoNC fluid.

Figure 5:
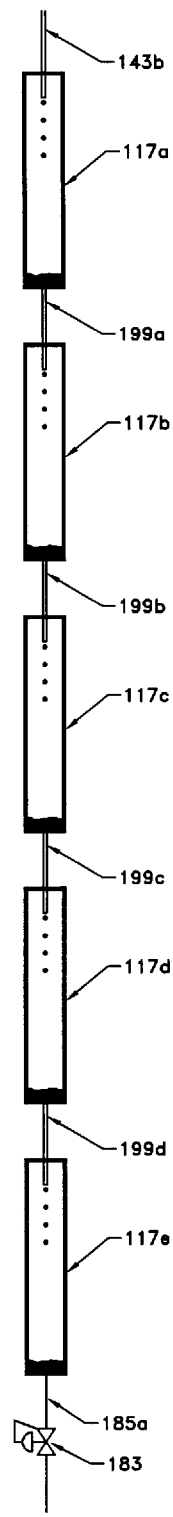
FIG. 5 is a schematic illustration of a multistage apparatus embodying features of the present invention.

In the alternative, as illustrated in FIG. 5, a plurality of laminar mixing vessels 117 a–e may be interposed for laminar mixing vessel 117 in apparatus 111. Each laminar mixing vessel 117 a–e is in communication with another through suitable conduits 199 a–d. The total inactivation of virus in a sample is approximately equal to the inactivation per stage or cycle, times the number of cycles or stages, plus the final release of pressure.

Preferably, the sample injection assembly 113, SCoCoNC injection assembly 115, laminar mixing vessel 117 and sample withdrawal assembly 119 are maintained at constant temperature by copper tubing jackets 197a and 197b and temperature device 197 control such as a Neslab bath.

In operation, the SCoCoNC fluid injection assembly 115 and laminar mixing vessel 117 are charged with SCoCoNC fluid. Three-way valve 127 is placed in communication with sample injection assembly 113 and laminar mixing vessel 117. Sample is pumped into Laminar mixing vessel 117 at a constant flow of 0.2 ml/minute. After a few ml are received in laminar mixing vessel 117, back pressure regulation 183 is adjusted to release sample and SCoCoNC fluid mixtures to the defoaming chamber 181. The mixture is degassed and sample removed through port 195.

EXAMPLES

In the examples described herein, samples of a recombinant murine C-type retrovirus were prepared as follows. The cell line Psi-2 (Mann et al., 1983, Cell 33:153–159), which produces defective Moloney murine leukemia virus particles (particles that lack viral nucleic acid, but are otherwise wild type), was transfected with plasmid DNA consisting of the retrovirus vector LNCX (Miller and Rosman, 1989, Biotechniques 7:980–990) that had previously been modified by the insertion of a chimeric beta-tubulin gene (Bond et al., 1986, Cell 44:461–468) into the Stu 1 site of the LNCX vector. Clonal cell lines stably expressing the transfected DNA were derived and maintained as virus-producing stocks. By packaging the RNA produced by the transfected DNA into the defective particles, these cells produce infectious particles that are entirely normal with respect to overall structure, stability, and mode of infection, but containing the plasmid-derived rather that the wild type, genetic material (Mann et al., Ibid).

Because the LNCX sequences contain the antibiotic resistance gene neo and a suitable promoter, infection of cells with the recombinant retrovirus confers upon the cells resistance to the antibiotic Geneticin (G418). Conferral of Geneticin-resistance onto cells and their progeny was therefore used as the property by which virus titers were determined. Specifically, virus stocks were prepared by culturing the virus-producing cells at high density (50% confluence) in fresh culture medium (Dulebecco's modified Eagle's medium supplemented with 10% iron-supplemented calf serum [Hyclone, Inc., Logan, Utah], glutamine [1 mM], penicillin [100 U/ml] and streptomycin [100 ?m?g/ml]) for 18 hours at 37 C. in a humidified 5% CO2 atmosphere. Culture medium was harvested and passed through a 0.2 micron filter, divided into aliquots, quick frozen using a dry-ice/ethanol bath and stored at −80 C. Immediately before use, samples were warmed in a 37 C. water bath until just thawed and held on ice. Aliquots of a single virus preparation were used for the examples described below.

After virus-containing samples were mixed with other materials and treated as described in each of the examples, they were returned to ice, and assayed within 8 hours. Titer tests were performed by seeding 35 mm-style culture dishes with a mouse fibroblast line (NIH3T3 cells) in 3 ml of the culture medium described above at a density of 10,000 cells per well the evening before the assay was to be performed. Virus samples were added to the culture medium over the cells at various dilution from $10^0$ (undiluted) to $10^{-6}$. In some cases (where indicated), polybrene (Aldrich Chemical Co.) was added along with virus at a final concentration of 2 ?m?g/ml. Polybrene is a polycation that enhances the infectivity of retroviruses up to 100-fold, apparently by enhancing the adsorption of viral particles to cell surfaces; polybrene is commonly used in assaying mouse retrovirus titers. After addition of virus, test cells were returned to the incubator overnight, and then washed into fresh medium containing 1 mg/ml Geneticin. This medium was replenished 2–3 times over the following two weeks, after which the plates of cells were fixed (with 10% formalin in phosphate-buffered saline), stained with Coomassie Blue dye, washed in 25% ethanol, and air-dried. During the two weeks of growth, each virus-infected cell gives rise to a colony of Geneticin-resistant cells. Because the LNCX-genome does not encode the functions necessary to produce new virus particles, virus-infected particles do not spread infection to nearby cells. Therefore, all cells not infected during the initial overnight exposure to the virus remain sensitive to the antibiotic, and die during the two week incubation. Consequently, the number of colonies (as visualized by Coomassie blue staining) present at two weeks provides an accurate reflection of the number of infectious virus particles initially applied to the cells. In parallel with all examples shown, control experiments were performed to demonstrate that cells not exposed to virus produced no colonies at two weeks, and cells exposed to untreated virus produced the expected number of colonies.

The cause of toxicity has not yet been determined but may is involve any of at least four possible mechanisms:

Extraction of Viral Components

Critical fluids are excellent solvents. They can exhibit a liquid-like density and, at the same time, gas-like properties of diffusivity, viscosity and surface tension. The critical fluids may be penetrating cells and subcellular structures (exhibiting solubilization properties similar to those of organic liquids). For example, supercritical carbon dioxide at 3,000 psig and 40 C. has a density of 0.8 g/cc and behaves like an organic solvent with the diffusivity of a gas. Critical fluids have additional degrees of freedom over organics in that salvation capacity can be readily adjusted by changing density (via changes in temperature and/or pressure), and selectivity can be altered by the type and concentration of polar entrainers such as an alcohol. One virus component that might be disrupted by critical fluids is the viral envelope, which contains cell derived lipids.

Explosive Decompression

Upon depressurization, critical fluids exhibit large specific volume changes. For example, supercritical carbon dioxide will expand by a factor of approximately 400 fold when depressurized from 3,000 psig and 40 C. to atmospheric conditions. When depressurization is sufficiently rapid, explosive decompressive forces may play a role in disrupting microscopic structures.

Virus Particle Disintegration

The components of viruses (proteins, nucleic acid, and sometimes lipid) self-assemble inside cells to produce infectious viral particles. Noncovalent forces of protein aggregation are primarily responsible for holding these particles together. Under conditions of very high pressure (e.g. 20,000 psig and higher), protein-protein and protein-lipid interactions can be disrupted. Thus, it is possible that viral particles undergo partial or total disassembly under the conditions that we have used.

Chemical Modification

Under atmospheric conditions, most viruses are chemically quite stable. Under conditions of high pressure and in the presence of critical fluids, however, chemical reactions might occur that do not normally do so under atmospheric conditions at a significant rate. Examples of such reactions might be the oxidation of lipids (perhaps catalyzed by nitrous oxide), or the hydrolysis or chemical modification of nucleic acids, both of which might interfere with virus function. Chemical reactions involving proteins might also occur, although the remarkably mild effects of the viral inactivation process on bovine plasma (see below) suggest that proteins are relatively unaffected by the process.

In addition to demonstrating that critical fluids can be toxic to viruses, the impact of the critical fluid viral inactivation processes on biologically active proteins and small molecules were examined. If critical fluid inactivation is to be useful in destroying viruses in biological samples such as blood plasma, cell culture media, pharmaceutical substances, and substances derived using recombinant DNA techniques, the process must be relatively harmless to the beneficial components of those substances. Proteins are of the greatest concern in this regard, because these molecules are susceptible to denaturation by a host of factors including temperature, extremes of pH and ionic strength, drying, exposure to nonaqueous liquids or detergents, and even mechanical shear.

During the conduct of research on several other bioseparation processes utilizing critical fluids, we have subjected several natural and recombinant-DNA proteins were subjected to a variety of critical fluids under different conditions. Data suggests that there were no detectable changes in activity and structural conformation of recombinant growth hormone under conditions which are very similar to those in the examples given below.

In order to demonstrate that the conditions necessary for viral inactivation are not exceedingly harmful to the beneficial constituents of proteinaceous products, several experiments were conducted and are reported in Examples 1, 2, 3 and 4 below. Similar conditions were then utilized to inactivate viral particles in the presence of different levels of proteins; these experiments are reported in Examples 5, 6 and 7 below.

Examples of our disclosure are given below to show how variables such as critical fluid type, cosolvent concentration, temperature, pressure and time can effect reduction in viral activity and biological activity. It should be understood that the critical fluid viral inactivation process is not limited to the following examples which are presented to further illustrate the invention.

Example 1

Impact of Supercritical Carbon Dioxide and Nitrous Oxide on Bovine Plasma

In order to evaluate if critical fluid treatment would adversely affect the beneficial constituents of plasma, several experiments were carried out with bovine plasma. Aseptically collected bovine blood treated with an anticoagulant (sodium citrate) was centrifuged at a speed of 3,000 rpm for 30 minutes in a refrigerated centrifuge at 10 C. 75 ml of the decanted plasma was introduced into the apparatus shown as FIG. 1, contacted with the critical fluid at the conditions listed in the top half of Table 1 and then slowly decompressed to atmospheric conditions.

In this series of experiments, there were two controls—CFI-0 which is the untreated, unprocessed plasma, and CFI-3 which is processed in the critical fluid viral inactivation (CFI) apparatus without critical fluids. The latter control accounts for the mechanical impact of mixing on proteins and other beneficial constituents. The recovered samples were spun down in a refrigerated centrifuge at 3,000 rpm for 30 minutes at 10 C.; the clarified plasma was then sent out to Tufts University Veterinary Diagnostic Laboratory, Boston, Mass. for analysis. The results of this analysis are summarized in the bottom half of Table 1 below:

TABLE 1

IMPACT OF CRITICAL FLUID CARBON DIOXIDE
AND NITROUS OXIDE ON BOVINE PLASMA

| PARAMETER | CFI-0 | CFI-1 | CFI-2 | CFI-3 |
| --- | --- | --- | --- | --- |
| Critical Fluid | — | CO2 | N20 | — |
| Pressure (psig) | — | 4,000 | 4,000 | — |
| Temperature © | 4 | 40 | 40 | 40 |
| Time (mins) | — | 30 | 30 | 30 |
| Glucose (mg/dl) | 64 | 41 | 62 | 60 |
| BUN (mg/dl) | 17 | 17 | 17 | 18 |
| Protein (g/dl) | 6.9 | 5.1 | 6.5 | 6.7 |
| AKP (U/l) | 252 | 0 | 178 | 228 |
| LDH (U/l) | 1,458 | 38 | 1,011 | 1,428 |
| Albumin (g/dl) | 3.4 | 5.5 | 4.2 | 3.2 |
| CPK (U/l) | 547 | 44 | 199 | 432 |

BUN - Blood Urea Nitrogen
AKP - Alkaline Phosphatase
LDH - Lactic Dehydrogenase
CPK - Creatine Phosphokinase These data suggest that supercritical carbon dioxide had an adverse impact on several constituents of the bovine plasma, namely alkaline phosphatase (AKP), lactic dehydrogenase (LDH) and creatine phosphokinase (CPK). The data suggests that supercritical nitrous oxide had minor effects. Supercritical carbon dioxide may be the fluid of choice for the treatment of medical devices and apparatus where the preservation of protein bioactivity is of no importance.

Example 2

Impact of Pressure on Critical Fluid Nitrous Oxide on Bovine Plasma

A second set of runs was conducted with supercritical nitrous oxide at different pressures. Within 24 hours after treatment, a SMAC analysis was performed on the recovered plasma by Bioran Laboratories, Cambridge, Mass. All SMAC results were repeated and verified by Bioran Laboratories. The conditions of these runs and the results of the analysis are listed in Table 2 below:

TABLE 2

IMPACT OF PRESSURE ON CRITICAL FLUID
NITROUS OXIDE ON BOVINE PLASMA

| PARAMETER | CFI-00 | CFI-4 | CFI-5 | CFI-6 | CFI-7 |
| --- | --- | --- | --- | --- | --- |
| Critical Fluid | — | N2O | N2O | N2O | N20 |
| Pressure (psig) | — | — | 1,000 | 2,000 | 3,000 |
| Temperature © | 4 | 40 | 40 | 40 | 40 |
| Time (mins) | — | 30 | 30 | 30 | 30 |
| Glucose (mg/dl) | 77 | 148 | 149 | 155 | 153 |
| BUN (mg/dl) | 18 | 16 | 15 | 16 | 16 |
| Protein (g/dl) | 7.7 | 6.3 | 5.9 | 6.4 | 6.5 |
| AKP (U/l) | 24 | 30 | 30 | 34 | 35 |
| LDH (U/l) | 1,111 | 891 | 767 | 883 | 891 |
| Albumin (g/dl) | 2.5 | 2.4 | 2.4 | 2.6 | 2.5 |

TABLE 2-continued

IMPACT OF PRESSURE ON CRITICAL FLUID
NITROUS OXIDE ON BOVINE PLASMA

| PARAMETER | CFI-00 | CFI-4 | CFI-5 | CFI-6 | CFI-7 |
|---|---|---|---|---|---|
| Triglycerides (mg/dl) | 11 | 16 | 17 | 18 | 17 |
| Cholesterol (mg/dl) | 143 | 148 | 136 | 150 | 154 |

BUN - Blood Urea Nitrogen
AKP - Alkaline Phosphatase
LDH - Lactic Dehydrogenase
CPK - Creatine Phosphokinase At the end of the experiments, the mixture of critical fluid and bovine plasma was rapidly decompressed (at a rate around 100 psig/sec) and the critical fluid separated from the now treated plasma. The results suggest that supercritical nitrous oxide had little or no impact on blood urea nitrogen (BUN), AKP, LDH, albumin, triglycerides and cholesterol over the range of pressures tested, and there was little or no sensitivity to the level of pressure between 1,000 and 3,000 psig. Glucose values for experiments CFI-4 through CFI-7 are about twice that of the control CFI-00. The higher glucose levels could have been caused by the critical disruption of red blood cells which were not removed in the plasma preparation.

Example 3

Impact of Critical Fluid Type on Bovine Plasma

In this series of experiments, the critical fluid was varied; with the exception of the control—CFI-00—process conditions were 3,000 psig, 40° C. and 30 minutes. The critical fluids tested were nitrous oxide (N2O), ethylene (C2H4), ethane (C2H6), propane (C3H8), tri-fluoromethane (CHF3 or Fr-23), chlorodifluoromethane (CHClF2 or Fr-22). The conditions of these experiments and some relevant thermodynamic properties are listed in the top half of Table 3 below:

in the bottom half of Table 3. These results can be compared against values for the control in Table 2. Apart from the doubling of glucose concentration levels and some detrimental effects on LDH in CFI-7 through CFI-12, the first six critical fluids tested in Table 3 had a negligible impact on blood constituents.

Example 4

Impact of Residence Time and Operating Temperature on the Critical Fluid Treatment of Bovine Plasma The impact of residence time and operating temperature on some of the beneficial constituents of bovine plasma treated by SCF N2O at 3,000 psig is listed in Table 4 below:

TABLE 4

IMPACT OF RESIDENCE TIME
AND OPERATING TEMPERATURE ON THE CRITICAL
FLUID TREATMENT OF BOVINE PLASMA

| PARAMETER | CFI-00 | CFI-7 | CFI-14 | CFI-15 |
|---|---|---|---|---|
| Critical Fluid | — | N2O | N2O | N2O |
| Pressure (psig) | — | 3,000 | 3,000 | 3,000 |
| Temperature (°C) | 4 | 40 | 30 | 30 |
| Time (mins) | — | 30 | 30 | 5 |
| Glucose (mg/dl) | 77 | 153 | 74 | 74 |
| BUN (mg/dl) | 18 | 16 | 14 | 17 |
| Protein (g/dl) | 7.7 | 6.5 | 7.3 | 7.2 |
| AKP (U/l) | 24 | 35 | 30 | 29 |
| LDH (U/l) | 1,111 | 891 | 1,018 | 1,057 |
| Albumin (g/dl) | 2.5 | 2.5 | 2.5 | 2.6 |
| Triglycerides (mg/dl) | 11 | 17 | 13 | 10 |
| Cholesterol (mg/dl) | 143 | 154 | 134 | 137 |

BUN - Blood Urea Nitrogen
AKP - Alkaline Phosphatase
LDH - Lactic Dehydrogenase
CPK - Creatine Phosphokinase The data suggests that temperature more than time had an impact on SCF N2O treated bovine plasma. For example, both CFI-14 and CFI-15 which were conducted at 30 C. had

TABLE 3

IMPACT OF CRITICAL FLUID TYPE ON BOVINE PLASMA

| PARAMETER | CFI-7 | CFI-8 | CFI-9 | CFI-10 | CFI-11 | CFI-12 | CFI-13 |
|---|---|---|---|---|---|---|---|
| Critical Fluid | N2O | C2H4 | C2H6 | C3H8 | Fr-23 | Fr-22 | N2 |
| Crit. Press. (psia) | 1,051 | 731 | 709 | 616 | 701 | 722 | 493 |
| Crit. Temp. (°C) | 36.4 | 9.2 | 32.2 | 96.6 | 25.9 | 96.0 | −147.0 |
| Pressure (psig) | 3,000 | 3,000 | 3,000 | 3,000 | 3,000 | 3,000 | 3,000 |
| Temperature (°C) | 40 | 40 | 40 | 40 | 40 | 40 | 40 |
| Time (mins) | 30 | 30 | 30 | 30 | 30 | 30 | 30 |
| Glucose (mg/dl) | 153 | 157 | 156 | 161 | 166 | 132 | 68 |
| BUN (mg/dl) | 16 | 17 | 16 | 17 | 16 | 16 | 12 |
| Protein (g/dl) | 6.5 | 6.8 | 6.9 | 7.1 | 6.4 | 6.5 | 6.6 |
| AKP (U/l) | 35 | 34 | 33 | 35 | 26 | 24 | 24 |
| LDH (U/l) | 891 | 808 | 837 | 907 | 522 | 510 | 971 |
| Albumin (g/dl) | 2.5 | 2.7 | 2.5 | 2.6 | 2.7 | 2.8 | 2.3 |
| Triglycerides (mg/dl) | 17 | 19 | 18 | 18 | 30 | 29 | 11 |
| Cholesterol (mg/dl) | 154 | 154 | 152 | 152 | 124 | 134 | 128 |

BUN — Blood Urea Nitrogen
AKP — Alkaline Phosphatase
LDH — Lactic Dehydrogenase
CPK — Creatine Phosphokinase These solvents, with the exception of propane and Freon-22, are all supercritical at the tested conditions of 3,000 psig and 40° C. The results of explosive decompression experiments with these critical fluids and bovine plasma are listed negligible impacts on glucose, total protein and LDH versus CFI-7 which was conducted at 40 C. Also, there was no significant difference in the impact of CFI-14 and CFI-15 which had residence times of 30 and 5 minutes.

Example 5

Impact of Residence Time on Critical Fluid Viral Inactivation of Murine-C Retrovirus in Culture Medium Several tests were conducted with 30 ml of culture medium containing murine C-type retroviruses and supercritical nitrous oxide at approximately 3,000 psig and 40° C. These experiments (CFI-18, CFI-19, and CFI-20 listed in Table 5) were conducted at different residence times ranging from 5 to 121 minutes; CFI-21 in Table 5 was conducted with supercritical nitrogen at similar conditions of temperature and pressure for 30 minutes. Between each run, and as described above, the experimental apparatus was rinsed with sterile deionized water, sterilized with 70% ethanol through 7 and 0.5 micron filters, and again rinsed with sterile deionized, distilled water; the apparatus was then dried with filtered compressed nitrogen or air.

After each experiment, the recovered samples were halved; one half was spun down at 2,500 rpm for 10 minutes and the supernatant subjected to 0.45 micron filtration. Titer tests, ability to infect 3T3 fibroblasts and confer G418 resistance, were conducted on duplicate 2.3 ml samples at six different dilutions. The appropriate titers of recovered samples are listed in Table 5 and shown as a function of residence time in FIG. 4. The results indicate that supercritical nitrogen was relatively ineffective in inactivating the retrovirus whereas supercritical nitrous oxide was very effective in inactivating the retrovirus. The supercritical nitrogen results can be correlated with its inability to solubilize/liberate phospholipids as shown in FIG. 3. On the other hand, supercritical nitrous oxide rapidly inactivated the retrovirus in a period between 30 and 121 minutes.

TABLE 5

IMPACT OF RESIDENCE TIME ON CRITICAL FLUID VIRAL INACTIVATION OF MURINE-C RETROVIRUS IN CULTURE MEDIUM

| PARAMETER | Control | CFI-18 | CFI-19 | CFI-20 | CFI-21 |
|---|---|---|---|---|---|
| Critical Fluid | — | N2O | N2O | N2O | N2 |
| Pressure (psig) | — | 2,560 | 2,690 | 3,180 | 3,250 |
| Temperature © | 4 | 43 | 41 | 41 | 41 |
| Time (mins) | — | 30 | 5 | 121 | 30 |
| Titer (cfu/2.3 ml) | 5,000 | 10 | 50 | <5* | 3,000 |
| - log10 Reduction | N/A | 2.7 | 2.0 | >3.0 | 0.2 |

*Detection limit

Example 6

Impact of Critical Fluid Type and Cosolvent on the Viral Inactivation of Murine-C Retrovirus in Serum Several critical fluid viral inactivation experiments were conducted with murine-C retrovirus in serum. Proteins are known to have a protective effect on the viability of viruses. These experiments were thus conducted to evaluate the effectiveness of the critical fluid viral inactivation technique in a protein-rich medium. Murine-C retrovirus in culture medium was mixed 50/50 with serum (serum was a 50/50 mix of Hyclone fetal bovine serum and Hyclone iron supplemented calf serum) and divided into 5 equal aliquots. Experiments were conducted with several critical fluids—nitrous oxide (N2O), a nitrous oxide/2 mole % ethanol mixture, chlorodifluoromethane (CHClF2 or Fr-22) and propane (C3H8) at approximately 3,000 psig and 40 C. for a residence time of 30 minutes. One critical fluid experiment (CFI-26) was conducted at 60 C. These experiments are listed in Table 6. Several controls were conducted on samples which were not treated with critical fluids—one at 40 C., one at 40 C. with 2 mole % ethanol in the serum, and one at 60 C.

Titers were run on controls and recovered samples without polybrene enhancement (in duplicate at six dilutions) and with polybrene enhancement (in duplicate at four dilutions). The titer results indicate that 2 mole % ethanol does not affect the titer but that heating at 60 C. does destroy the retrovirus. The titer results presented in Table 6 are for polybrene enhanced determinations (these valves are consistent with titers determined without polybrene). The 40 C. control had a titer of 65,000 cfu/2.3 ml. The results listed in Table 6 indicate that the presence of protein did reduce the effectiveness of supercritical nitrous oxide by one to two orders of magnitude (compare CFI-27 in Table 6 to CFI-18 in Table 5). Also, 2 mole % ethanol had little or no impact on the effect of supercritical nitrous oxide. Freon-22, however, had a significant impact on murine-C retrovirus, reducing viral activity by some 3.2 log orders of magnitude after 30 minutes of contacting the serum.

TABLE 6

IMPACT OF CRITICAL FLUID TYPE AND COSOLVENT ON THE VIRAL INACTIVATION OF MURINE-C RETROVIRUS IN SERUM

| PARAMETER | Control | CFI-26 | CFI-27 | CFI-28 | CFI-29 | CFI-30 |
|---|---|---|---|---|---|---|
| Critical Fluid | — | N2O | N2O | N2O/EtOH | Fr-22 | C3H8 |
| Pressure (psig) | — | 3,000 | 3,000 | 3,000 | 3,000 | 3,000 |
| Temperature © | 40 | 60 | 40 | 41 | 41 | 41 |
| Time (mins) | — | 30 | 30 | 30 | 30 | 30 |
| Titer (cfu/2.3 ml) | 65,000 | <5* | 3,000 | 5,000 | 40 | 2,500 |
| - log10 Reduction | N/A | >4.1 | 1.4 | 1.1 | 3.2 | 1.4 |

*Detection limit

Example 7

Impact of Residence Time, Critical Fluid Type and Pressure on the Viral Inactivation of Murine-C Retrovirus in Serum Based on the results in Example 6, several experiments were conducted with Freon-22 at approximately 3,000 psig and 40° C. to determine the impact of residence time on viral reduction capability. The experiments, listed in Table 7, indicate that Freon-22 can, within the detection limits of the assay, eliminate viral activity within five minutes.

This example also indicates that pressure has a significant impact on the effectiveness of critical fluid viral inactivation. CFI-34 in Table 7 indicate that supercritical nitrous oxide at 5,000 psig and 40° C. for a residence time of 30 minutes inactivated the entire viral population (within the detection limits of the assay), while CFI-27 in Table 6 shows that supercritical nitrous oxide at 3,000 psig and 40° C. for a residence time of 30 minutes reduces virus activity by 1.4 logs.

TABLE 7

IMPACT OF RESIDENCE TIME, CRITICAL FLUID TYPE AND PRESSURE ON THE VIRAL INACTIVATION OF MURINE-C RETROVIRUS IN SERUM

| PARAMETER | Control | CFI-31 | CFI-32 | CFI-33 | CFI-34 | CFI-35 |
|---|---|---|---|---|---|---|
| Critical Fluid | — | Fr-22 | Fr-22 | Fr-22 | N2O | N2 |
| Pressure (psig) | — | 3,000 | 3,000 | 3,000 | 5,000 | 3,000 |
| Temperature (°C.) | 40 | 40 | 40 | 41 | 41 | 41 |
| Time (mins) | — | 5 | 15 | 60 | 30 | 60 |
| Titer (cfu/2.0 ml) | 20,000 | <5* | 5 | <5* | <5* | 3,750 |
| − log10 Reduction N/A | | >3.6 | 3.6 | >3.6 | >3.6 | 0.7 |

*Detection limit

Example 8

Several tests were performed with murine-C retrovirus (MuLV) and nitrous oxide at 2,200 psig and 22° C. MuLV, an enveloped or lipid-encased virus which has an outer diameter of approximately 100 nanometers (nm), is often used as a surrogate for the human immunodeficiency virus (HIV). In a typical experiment, the selected proteinacious matrix (including fetal bovine serum, plasma or plasma products, such as immunoglobulins) is spiked with a particular virus and treated using the bench scale SCoCoNC equipment shown in FIG. 5 or appropriate modifications under tightly controlled conditions with defined SCoCoNC, temperature and pressure. The residence time of droplet in a single stage laminar mixing vessel unit is approximately 20 seconds; the residence time in a two-stage unit is approximately 40 seconds. Treated samples are collected either in bulk at the end of a complete run or at specified times during the run. Control and treated materials are analyzed for residual virus. Samples are also evaluated with respect to total protein and biological properties of the proteins.

Selected results are presented in Table 8 below.

TABLE 8

SCoCoNC Inactivation of Murine Leukemia Virus (MuLV) with Nitrous Oxide in Laminar Flow Injection Unit

| Parameters | CFI-286 | CFI-380 | CFI-381 | CFI-464 |
|---|---|---|---|---|
| Pressure (psig) | 2,000 | 2,000 | 2,000 | 2,000 |
| Temperature (°C.) | 22 | 22 | 22 | 22 |
| Time (mins) | <1 | <1 | <1 | <1 |
| Titer Control | $1 \times 10_{4.0}$ | $1 \times 10_{5.0}$ | $1 \times 10_{3.0}$ | $1 \times 10^{5.5}$ |
| Titer After | $1 \times 10_{3.0}$ | $1 \times 10_{3.7}$ | $1 \times 10_{1.0}$ | $0 \times 10^{0.0*}$ |
| − log10 reduction | 1.0 | 2.3 | 2.0 | >5.5 |
| No. of Stages | 0 | 1 | 1 | 2 |

*below minimum detection level

CFI-286 was performed by directly passing the pressurized stream through the back pressure regulator without having contacted that stream with nitrous oxide. This zero (0) stage experiment resulted in about 1 log inactivation. Experiments CFI-380 and CFI-381 were performed in a single stage laminar mixing vessel in the presence of nitrous oxide under similar conditions of temperature and pressure for less than one minute. These experiments resulted in about 2 logs of MuLV inactivation in about 20 seconds. Experiment CFI-464 was conducted in a two-stage laminar mixing vessel with nitrous oxide under identical conditions of temperature and pressure. This two-stage experiment resulted in greater than 5.5 logs of MuLV inactivation. The two stage unit inactivated about twice the amount of MuLV inactivated by the one stage unit plus one log due to the decompression valve in a residence time of less than one minute. This discovery shows that the laminar flow SCoCoNC unit is effective in very short times (<20 seconds) and is directly scalable on a per stage basis so that the levels of inactivation can be controlled by the number of stages in place.

Example 9

Several tests were performed with vesicular stomatitis virus (VSV) and nitrous oxide at 2,200 psig and 22° C. VSV is an enveloped virus with a distinctive bullet shape (50–95 nm×130–380 nm). VSV is a member of the Rhabdovirus family. VSV possess a negative-strand RNA genome and codes for only five proteins which are found in the virion. VSV is an animal pathogen which grows well in cell culture; the host cell for VSV is the A549 cell line. Quantitation was carried out using an infectivity titration assay (50% end point referred to as TCID50); titration was performed on overnight cultures of A549 host cells. Selected results are presented in Table 9 below.

TABLE 9

SCoCoNC Inactivation of Vesicular Stomatitis Virus (VSV) with Nitrous Oxide in Laminar Flow Injection Unit

| Parameters | CFI-574 | CFI-588 |
|---|---|---|
| Pressure (psig) | 4,000 | 4,000 |
| Temperature (°C.) | 40 | 40 |
| Time (mins) | <1 | <1 |
| Titer Control | $1 \times 10_{5.0}$ | $1 \times 10^{5.5}$ |
| Titer After | $1 \times 10_{2.5}$ | $0 \times 10^{0.0*}$ |
| −log10 reduction | 2.5 | >5.5 |
| No. of Stages | 1 | 2 |

In a two stage unit, the SCoCoNC process achieved about twice the inactivation shown in the single stage unit. Other data for the inactivation of VSV by nitrous oxide in shows that inactivation increased with increases in temperature and pressure. An average of 4 logs of inactivation were achieved with nitrous oxide at a pressure of 5,000 psig and a temperature of 40° C. At the same pressure but a lower temperature of 22° C., about one half or 2 logs of inactivation are achieved suggesting that the rate of inactivation is very sensitive to temperature. At lower temperatures (15° C. and 22° C.), inactivation of VSV does not appear to be very sensitive to pressure.

Example 10

Several experiments were conducted with encephalomyocarditis (EMC), a tough, prototypical non-enveloped or protein-encased virus with different SCoCoNC at different pressures and temperatures in the single stage laminar flow unit. EMC, a member of the Picornaviridae family, is a positive-strand RNA virus which is isohedral. EMC is icosahedral in shape with a size of 20 to 30 nanometers. EMC, an animal virus which is non-pathogenic to man, is often used as a marker virus in process validation studies. Other viruses of major concern belonging to the Picornaviridae family include Hepatitis A, Polioviruses and Parvoviruses. Quantitation was carried out using an infectivity titration assay (50% end point referred to as TCID50) on susceptible host cells A549, a cell line derived from human carcinoma tissue. A sample of the experimental results are listed in Table 10.

TABLE 10

SCoCoNC Inactivation of Encephalomyocarditis (EMC)
with Freon-22 in Single-Stage Laminar Flow Injection Unit

| Parameters | CFI-887 | CFI-551 | CFI-914 | CFI-915 |
|---|---|---|---|---|
| Pressure (psig) | 3,000 | 3,000 | 3,000 | 3,000 |
| Temperature (°C.) | 50 | 50 | 50 | 50 |
| Time (mins) | <1 | <1 | <1 | <1 |
| Titer Control | $1 \times 10_{5.6}$ | $1 \times 10_{5.6}$ | $1 \times 10_{5.2}$ | $1 \times 10^{5.2}$ |
| Titer After | $1 \times 10_{-0.3}$ | $1 \times 10_{0.2}$ | $1 \times 10_{-0.5}$ | $1 \times 10^{-0.4}$ |

TABLE 10-continued

SCoCoNC Inactivation of Encephalomyocarditis (EMC)
with Freon-22 in Single-Stage Laminar Flow Injection Unit

| Parameters | CFI-887 | CFI-551 | CFI-914 | CFI-915 |
|---|---|---|---|---|
| -$\log_{10}$ reduction | 5.9 | 5.4 | >5.7* | 5.6 |
| No. of Stages | 1 | 1 | 1 | 1 |

Figure 6:
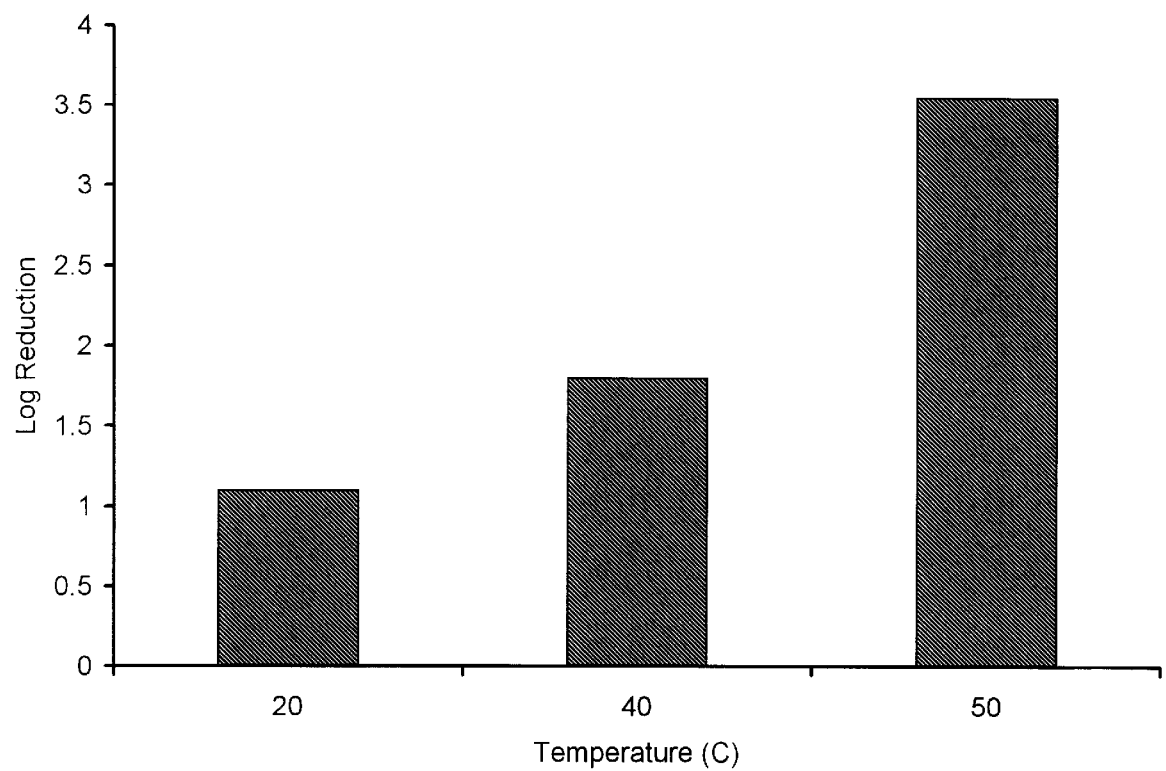
FIG. 6 illustrates in bar graph form the log reduction in virus vs temperature at 5,000 psig; and, FIG. 7 illustrates in bar graph form the log reduction in virus vs pressure at 50° C.
Figure 7:
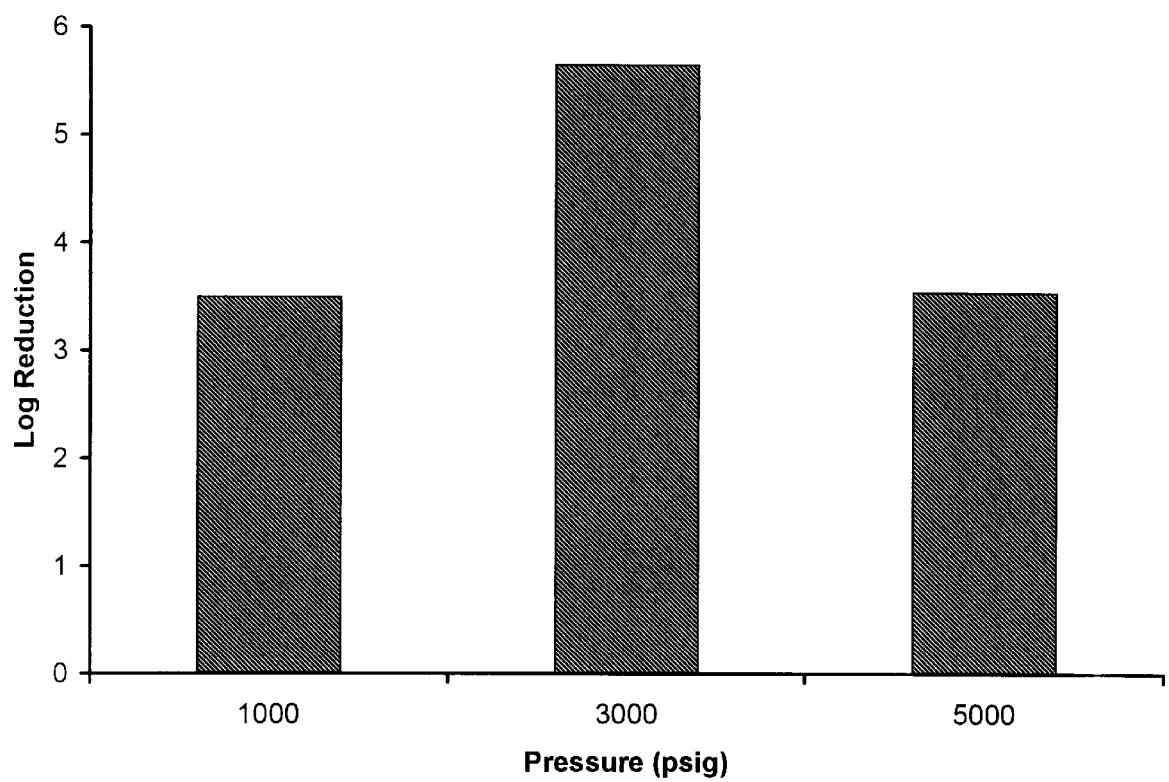

As shown in Table 10 above, approximately six logs of the tough, prototypical non-enveloped EMC virus were inactivated by Freon-22 in a single stage laminar mixing vessel in less than 20 seconds. Other experiments in the single-stage, laminar mixing vessel indicate the following: (1) EMC inactivation (on the average 5.7 logs) was optimal with Freon-22 at 3,000 psig and 50° C. in a single stage laminar flow unit. This was consistently confirmed in at least four experiments, CFI-887, CFI-889, CFI-914 and CFI-915; (2) As shown in FIG. 6, inactivation increases with temperature increase—~1 log for every 10° C. increase in temperature with Freon-22 at 5,000 psig; and (3) As shown in FIG. 7, inactivation is greatest at a pressure of 3,000 psig with Freon-22 at 50° C. This result was totally unanticipated since it was expected that further increases in pressure would result in higher explosive decompression forces resulting in greater virus kill.

Example 11

The inactivation of several viruses in Freon-22 at 3,000 psig and 50° C., conditions which appear to be optimum for inactivating EMC, are listed in Table 11. All experiments were conducted with an Isco syringe pump with the exception of CFI-908 and CFI-909, for Hepatitis A (HAV) which were conducted with the Eldex piston pump at 4 ml/min. The latter course of action was taken because, within the constraints of our current equipment configuration, the Eldex pump can be operated in the laminar flow safety cabinet which would contain any aerosols generated.

TABLE 11

SCoCoNC INACTIVATION OF DIFFERENT VIRUSES
BY FREON-22 @ 3,000 PSIG AND 50° C.
IN SINGLE-STAGE LAMINAR FLOW INJECTION UNIT

| CFI No. | Virus | Matrix | Family | Genome | Size | Capsid | - $\log_{10}$ Kill |
|---|---|---|---|---|---|---|---|
| 916 | Adeno | FBS | Adenoviridae | ds-DNA | 70–90 | Non-Env. | >5.3 |
| 917 | Adeno | FBS | Adenoviridae | ds-DNA | 70–90 | Non-Env. | >5.1 |
| 918 | Polio | FBS | Picornaviridae | ss-RNA | 18–26 | Non-Env. | 4.1 |
| 919 | Polio | FBS | Picornaviridae | ss-RNA | 18–26 | Non-Env. | 4.2 |
| 908 | HAV | FFP | Picornaviridae | ss-RNA | 24–30 | Non-Env. | 1.3 |
| 909 | HAV | FFP | Picornaviridae | ss-RNA | 24–30 | Non-Env. | 1.0 |
| 898 | Reo | FBS | Reoviridae | ds-RNA | 65–75 | Non-Env. | 0.9 |
| 889 | Reo | FBS | Reoviridae | ds-RNA | 65–75 | Non-Env, | 1.0 |
| 904 | VSV | FBS | Rhabdoviridae | ss-RNA | 60–180 | Enveloped | >6.5 |
| 905 | VSV | FBS | Rhabdoviridae | ss-RNA | 60–180 | Enveloped | >6.6 |
| 906 | Sindbis | FBS | Togaviridae | ss-RNA | 60–70 | Enveloped | >6.5 |
| 907 | Sindbis | FBS | Togaviridae | ss-RNA | 60–70 | Enveloped | 6.5 |
| 902 | TGE | FBS | Coronaviridae | ss-RNA | 80–130 | Enveloped | >2.5 |
| 903 | TGE | FBS | Coronaviridae | ss-RNA | 80–130 | Enveloped | >2.6 |
| 900 | BVD | HS | Togaviridae | ss-RNA | 60–70 | Enveloped | 2.3 |
| 901 | BVD | HS | Togaviridae | ss-RNA | 60–70 | Enveloped | 2.3 |

The data listed in Table 4 indicates the following trends:

All of the non-enveloped virus, Human Adenovirus, Type 5 was consistently inactivated (>5.1 and 5.3 logs) with Freon-22 at 3,000 psig and 50° C.

In excess of four logs of inactivation (4.1 and 4.2) were achieved with the very small and tough Poliovirus which is nonenveloped protein encased, in less than 20 seconds with Freon-22 at 3,000 psig and 50° C.

Approximately one log of inactivation was obtained for Hepatitis A (HAV) virus with Freon-22 at 3,000 psig and 50° C.

Consistent one log kill (0.9 and 1.0 logs) was achieved with the tough, non-enveloped Reovirus with Freon-22 at 3,000 psig and 50° C.

Complete inactivation of greater than six logs (>6.5 and >6.6) was obtained with Vesicular Stomatitis Virus (VSV) in Freon-22 at 3,000 psig and 50° C. This was the greatest single-stage inactivation of VSV in a continuous laminar mixing vessel SCoCoNC apparatus.

Complete or near-complete inactivation of greater than six logs (>6.5 and 6.5) was also obtained with Sindbis in Freon-22 at 3,000 psig and 50° C. This was the greatest inactivation of Sindbis under any conditions or in any SCoCoNC apparatus.

Complete inactivation of greater than 2 logs (>2.5 and >2.6) was achieved with TGE in Freon-22 at 3,000 psig and 50° C. The viral titer of the TGE used was low so that TGE inactivation could have been better than suggested by the results.

Example 12

From the data listed and discussed in the examples above, Freon-22 (hydrodifluorochloromethane—$CHClF_2$) appears to have very virucidal properties for both major classes of viruses, enveloped and non-enveloped. Relative to other chlorofluorcarbons such as Freon-11 and Freon-12, which are being banned by the 1988 Montreal protocol, Freon-22 is very stable and only has a slight ozone depletion potential (0.05 ODP) because it has a hydrogen atom in its structure. Alternate refrigerants were evaluated as to effectiveness on the prototypical, non-enveloped EMC virus at conditions found optimal for Freon-22. The thermodynamic properties of Freon-22 and the tested alternate refrigerants are listed in Table 12. The results of the comparative first steps are listed in Table 13.

TABLE 12

THERMODYNAMIC PROPERTIES OF SELECTED FLUOROCARBONS

| Generic Name | Chemical Formula | Critical Temperature $T_c$ © | Critical Pressure $P_c$ (psig) | Dipole Moment |
|---|---|---|---|---|
| Freon-22 | CHClF2 | 96.0 | 707.2 | 1.4 |
| Freon-23 | CHF3 | 25.9 | 686.5 | 1.6 |
| HCFC-123 | CF3CHCl2 | 183.6 | 532.0 | 1.36 |
| HCFC-124 | CHClFCF3 | 122.2 | 524.5 | 1.47 |
| HCFC-134a | CH2FCF3 | 101.1 | 574.2 | 2.06 |

From the comparison in Table 13, Freon-23 (trifluoromethane—$CHF_3$) appears to be the best alternate to Freon-22. On the average, Freon-23 inactivated~3 logs (2.2 and 3.5) versus ~6 logs (5.9, 5.4,>5.7 and 5.6) of EMC at similar conditions of temperature (50° C.) and pressure (3,000 psig). Per the listing of thermodynamic properties in Table 11, Freon-23 appears to be an excellent SCoCoNC candidate because: (I) it is non-chlorinated (the chlorine component of chlorofluorocarbons is thought to be responsible for their negative impact on the ozone layer): (ii) has a low critical temperature of 25.9° C. (allows operation close to critical conditions while minimizing thermal denaturation of biological proteins); and (iii) has a relatively large dipole moment of 1.6 debyes (has a large potential of solubilizing polar lipids and fats)

TABLE 13

SCoCoNC INACTIVATION OF ENCEPHALOMYOCARDITIS (EMC) VIRUS IN SINGLE-STAGE LAMINAR FLOW INJECTION UNIT WITH DIFFERENT FLUOROCARBONS

| CFI No. | Virus | Matrix | Critical Fluid | Mixing | Time (mins) | Press (psig) | Temp (°C.) | $-\log_{10}$ Kill |
|---|---|---|---|---|---|---|---|---|
| 887 | EMC | FBS | Fr-22 | Laminar | 0.33 | 3,000 | 50 | 5.9 |
| 889 | EMC | FBS | Fr-22 | Laminar | 0.33 | 3,000 | 50 | 5.4 |
| 914 | EMC | FBS | Fr-22 | Laminar | 0.33 | 3,000 | 50 | >5.7 |
| 915 | EMC | FBS | Fr-22 | Laminar | 0.33 | 3,000 | 50 | 5.6 |
| 926 | EMC | FBS | HFC-134a | Laminar | 0.33 | 3,000 | 50 | 1.3 |
| 927 | EMC | FBS | HFC-134a | Laminar | 0.33 | 3,000 | 50 | 0.1 |
| 933 | EMC | FBS | HFC-134a | Laminar | 0.33 | 3,000 | 50 | 0.6 |
| 932 | EMC | FBS | HFC-134a | Laminar | 0.33 | 5,000 | 50 | 0.3 |
| 928 | EMC | FBS | Fr-124 | Laminar | 0.33 | 3,000 | 50 | 0.5 |
| 929 | EMC | FBS | Fr-124 | Laminar | 0.33 | 3,000 | 50 | 0.4 |
| 930 | EMC | FBS | Fr-23 | Laminar | 0.33 | 3,000 | 50 | 2.2 |
| 931 | EMC | FBS | Fr-23 | Laminar | 0.33 | 3,000 | 50 | 3.5 |

Example 13

A set of experiments conducted to find optimal conditions for Freon-23 are listed in Table 14 below.

TABLE 14

SCoCoNC INACTIVATION OF ENCEPHALOMYOCARDITIS (EMC) VIRUS IN SINGLE-STAGE LAMINAR FLOW INJECTION UNIT WITH FREON-23 AT DIFFERENT CONDITIONS OF T & P

| CFI No. | Virus | Matrix | Critical Fluid | Mixing | Time (mins) | Press (psig) | Temp (°C.) | $-\log_{10}$ Kill |
|---|---|---|---|---|---|---|---|---|
| 936 | EMC | FBS | Fr-23 | Laminar | 0.33 | 1,000 | 50 | 2.7 |
| 937 | EMC | FBS | Fr-23 | Laminar | 0.33 | 1,000 | 50 | 3.5 |
| 930 | EMC | FBS | Fr-23 | Laminar | 0.33 | 3,000 | 50 | 2.2 |
| 931 | EMC | FBS | Fr-23 | Laminar | 0.33 | 3,000 | 50 | 3.5 |
| 934 | EMC | FBS | Fr-23 | Laminar | 0.33 | 5,000 | 50 | 2.7 |
| 935 | EMC | FBS | Fr-23 | Laminar | 0.33 | 5,000 | 50 | 3.1 |
| 938 | EMC | FBS | Fr-23 | Laminar | 0.33 | 3,000 | 26 | 0.2 |
| 943 | EMC | FBS | Fr-23 | Laminar | 0.33 | 3,000 | 37 | 0.0 |
| 941 | EMC | FBS | Fr-23 | Laminar | 0.33 | 5,000 | 58 | 4.6 |
| 931 | EMC | FBS | Fr-23 | Laminar | 0.33 | 5,000 | 58 | 4.5 |

Interestingly, the data for CFI-936, 937, 930, 931, 934 and 935 suggest that the inactivation of the tough, non-enveloped EMC virus by Freon-23 is independent of pressure over the narrow range of pressures tested (1,000 to 5,000 psig) at 50° C. This finding is very significant since operating a low pressure would significantly reduce the initial capital as well as operating costs of SCoCoNC CFI viral inactivation equipment. This data differs from that of Freon-22 which indicate the inactivation of EMC by Freon-22 appears to have a maxima at 3,000 psig over the same range of pressure.

The data in Table 14 indicates that the inactivation of EMC by Freon-23 is very sensitive to temperature, with little or no inactivation at lower temperatures (26° C. and 37° C.) and improved inactivation at 58° C. The data sets for both Freon-22 and Freon-23 indicate that inactivation of EMC increases with temperature.

Example 14

Single-stage and two-stage SCoNoNC experiments on EMC with Freon-22 are listed. The experiments, performed at 5,000 psig and 50° C., were based on initial EMC viral inactivation results at these conditions in the single-stage CFI unit (CFI-882 and CFI-883).

TABLE 15

SCoCoNC Inactivation of Encephalomyocarditis (EMC) with Freon-22 in Single-Stage and Two-Stage Laminar Flow Injection Units

| Parameters | CFI-882 | CFI-883 | CFI-894 | CFI-895 |
|---|---|---|---|---|
| Pressure (psig) | 5,000 | 5,000 | 5,000 | 5,000 |
| Temperature (°C.) | 50 | 50 | 50 | 50 |
| Time (mins) | <1 | <1 | <1 | <1 |
| Titer Control | $1 \times 10_{5.7}$ | $1 \times 10_{5.5}$ | $1 \times 10_{5.5}$ | $1 \times 10^{5.8}$ |
| Titer After | $1 \times 10_{2.1}$ | $1 \times 10_{2.0}$ | $1 \times 10_{0.6}$ | $1 \times 10^{1.6}$ |
| $-\log_{10}$ reduction | 3.6 | 3.5 | 4.9 | 4.2 |
| No. of Stages | 1 | 1 | 2 | 2 |

The data listed in Table 15 indicate that over four logs of inactivation (4.9 and 4.2 logs) was obtained with EMC in the two-stage CFI unit. In the single-stage unit (CFI-882 and CFI-883) 3.6 and 3.5 logs were obtained. The second stage appears to add an average of one log of inactivation.

Example 15

Several aliquots of a hyper-immunoglobulin were treated in a single stage laminar flow injection unit under various conditions of temperature (20° C. to 40° C.) and pressure (3,000 to 4,000 psig) with Supercritical nitrous oxide. Biochemical and biological analysis of the SCoCoNC treated samples were carried out and compared to a non-processed sample for molecular integrity and biological activity. The results of some of the analyses are tabulated in Table 16 below:

TABLE 16

ScoCoNC CFI Treatment of Hyper-Immunoglobulin in Single-Stage Laminar Flow Injection Unit

| CFI No. | HPLC-SEC (%) | Anti-Complementary | Protein (mg/ml) | ELISA MEP Abs |
|---|---|---|---|---|
| 595A | 104.3 | >1.81 | 18.00 | 351.4 |
| 595B | 99.7 | >1.78 | 17.84 | 385.4 |
| 596 | 108.1 | >1.78 | 17.78 | 346.2 |
| 597A | 101.4 | >1.83 | 18.27 | 349.7 |
| 597B | 92.7 | >1.77 | 17.65 | 313.8 |
| 598 | 93.7 | >1.76 | 17.58 | 325.8 |
| 599A | 94.7 | >1.74 | 18.14 | 379.5 |
| 599B | 95.2 | >1.74 | 17.39 | 370.8 |
| 600 | 93.1 | >1.82 | 18.20 | 374.2 |

Protein and anti-MEP antibodies content were determined by Bradford assay and ELISA assay, respectively, and were consistent with experimental control data. Molecular integrity of the treated samples was determined by reducing and non-reducing SDS-PAGE, HPLC-SEC, and Anti-complementary activity. The SDS-PAGE analysis of the experimental control and the treated process samples display similar banding patterns. The processed samples exhibited no significant aggregate or fragment bands, as compared to the experimental control. Repeated HPLC-SEC analyses showed that the treated samples exhibited similar chromatographic profiles to the untreated at 280 nm, and that there did not appear to be any significant aggregation or fragmentation. The process samples showed no significant aggregate formation that could be detected by the anti-complimentary activity, relative to the experimental control. Biological activities of the treated samples were measured by the Opsonophagocytosis Potency assay. All treated samples appear to exhibit higher specific opsonic activities than the experimental control.

Example 16

Several aliquots of an intravenous immunoglobulin were treated in a single stage laminar flow injection unit under various conditions of temperature (22° C. to 50° C.) and pressure (2,000 to 5,000 psig) with Supercritical Freon-22. Biochemical and biological analysis of the SCoCoNC treated samples were carried out and compared to a non-processed sample for molecular integrity and biological activity. The results of some of the analyses are tabulated in Table 17 below:

TABLE 17

SCoCoNC CFI Treatment of Ixnmunoglobulin (IV) in Single-Stage Laminar Flow Injection Unit

| CFI No. | RSV | POLIO | MEASLES | TETANUS | DIPHTHERIA |
|---|---|---|---|---|---|
| Control | 2186 | 2.4 | 1.3 | 311 | 4.8 |
| 752 | 2262 | 2.4 | 1.3 | 306 | 4.8 |
| 753 | 1870 | 2.4 | 1.3 | 285 | 4.8 |
| 754 | 2491 | 1.6 | 1.8 | 286 | 4.8 |
| 755 | 2142 | 1.6 | 1.5 | 290 | 4.8 |
| 756 | 982 | 0.8 | 1.4 | 295 | 4.8 |
| 757 | 1424 | 1.5 | 1.1 | 303 | 4.8 |

Antibody assays to asses IgG antigen binding and antibody effect or functions include: (1) neutralization of RSV, polio and measles viruses; (2) neutralization of tetanus and diphtheria bacterial toxins; and (3) ELISA measurement of antigen binding. In most cases, there was no significant difference between the SCoCoNC treated samples and the control. HPLC, Nephalometry and Anti-Complimentary activity assays all indicated that the treated samples had retained their molecular integrity.

Example 17

Preliminary SCoCoNC experiments were conducted on fresh porcine plasma in order to evaluate the impact of CFI conditions on coagulation factors. Fresh, citrated porcine whole blood was shipped on wet ice by an overnight express delivery service from Pel-Freez Biologicals, Rogers, Ark. The whole blood was centrifuged to separate the red blood cells from the plasma which was snap-frozen and stored at −80 C. The fresh, frozen porcine plasma was thawed at 30 C. and treated in the single stage laminar mixing vessel unit with nitrous oxide at 21 C. and 1,200 psig at different sample flowrates of 8(A), 8(B), 2(C), and 6(D) ml/minute. Control, untreated, and treated samples were stored at −80 C. prior to analysis. When ready to be analyzed, samples were thawed and analyzed for total protein, pH, enzymes, coagulation proteins, prothrombin and activated prothrombin times—all of which were tested in duplicate. The data, listed in Table 18, indicate little or no change in pH, fibrinogen, Factor VIII or Factor XI after SCoCoNC treatment. Prothrombin and activated prothrombin times of SCoCoNC treated samples were within ±3.0 seconds of the control time.

TABLE 18

SCoCoNC CFI Treatment of Fresh Frozen Porcine Plasma in Single-Stage Laminar Flow Injection Unit

| | pH | % Fibrinogen | % Factor VIII | % Factor XI |
|---|---|---|---|---|
| Control | 7.75 | 100 | 100 | 100 |
| Treated Sample A | 7.40 | 120 | 106 | 115 |
| Treated Sample B | 7.83 | 113 | 140 | 101 |
| Treated Sample C | 8.03 | 80 | 106 | 108 |
| Treated Sample D | 7.95 | 113 | 122 | 118 |

Example 18

Several experimental runs were performed on fresh frozen (human) plasma (FFP)in the single-stage laminar flow SCoCoNC unit with nitrous oxide ($N_2O$). Temperature and pressure were varied for each experimental run. All SCoCoNC treated samples, as well as untreated time and temperature controls, mechanical controls (sample pumped through the unit at a specified temperature and at no pressure and without any critical fluid), and pretreated controls were analyzed for protein integrity. Protein integrity was measured by the Pierce BCA protein assay, Activated Prothrombin Time (APTT), pH, and Factor VIII. A sample of these results are presented in Table 19.

TABLE 19

Impact of SCoCoNC CFI on Fresh Frozen Human Plasma in Single-State Laminar Flow Injection Unit

| Parameters | CFI-676 | CFI-679 |
|---|---|---|
| Pressure (psig) | 2,000 | 5,000 |
| Temperature (°C.) | 37 | 15 |
| Time (mins) | <1 | <1 |
| % Factor VIII | 87 | 84 |
| % Total Protein | 94 | 100 |

As shown in Table 19, Factor VIII protein recovery was well above 80% of untreated time and temperature controls. Controle experiments suggest these losses resulted from mechanical factors such as pumping and/or friction losses. Hydrogen ion concentration and total proteins of SCoCoNC treated FFP do not appear to be significantly adversely affected. Other testing indicated that the SCoCoNC process had little or no effect on sensitive blood plasma proteins. Recovery of protein activity in comparison to the time and temperature controls ranged 76% and 92% for Factor VIII, 85% and 92% for $a_1$-PI, and 91% and 95% for ATIII. Recovery of protein was worst at 15° C./2,500 psig, and better at 37° C./5,000 psig. In conclusion, treatment of source human plasma with SCoCoNC appears to produce minimal damage to plasma proteins.

Given the above disclosure and examples, variations and equivalents will be readily apparent to those skilled in the art without departing from the spirit and scope of the invention. Accordingly, it is intended that the examples be for illustration purposes only; variations and equivalents are intended to be included within the scope of the following claims.

We claim:

1. A method of inactivating one or more virions in a fluid containing a biological material potentially associated with a virion comprising:

a) contacting a fluid containing a biological material with a critical, supercritical or near critical fluid by introducing said fluid containing a biological material into a vessel which contains said critical, supercritical or near critical fluid, under nonturbulent conditions which have a Reynolds Number less than or equal to 2,000 wherein said contacting is under conditions sufficient to inactivate the virion if present; and, b) removing said critical, supercritical or near critical fluid from said fluid containing said biological material and said virion, if present, to render said virion inactive.

2. The method of claim 1, wherein said contacting is performed with a nozzle injecting said material into a vessel containing said supercritical, critical or near critical fluid.

3. The method of claim 2, wherein said nozzle releases droplets or a stream of sample.

4. The method of claim 1 wherein said material comprises a biological substance selected from the group consisting of proteins, and biologically active small molecules.

5. The method of claim 1 wherein said critical, supercritical or near critical fluid has a temperature in the range of approximately 0° C. to 100° C.

6. The method of claim 1 wherein said critical, supercritical or near critical fluid has a temperature in the range of approximately 4° C. to 60° C.

7. The method of claim 1 wherein said critical, supercritical or near critical fluid is selected from one or more compounds of the group consisting of fluorocarbons, and alkanes.

8. The method of claim 7 wherein said fluorocarbons is selected from one or more compounds of the group consisting of chlorodifluoromethane and trifluoromethane.

9. The method of claim 7 wherein said alkanes is selected from one or more compounds of the group consisting of ethylene, propane and ethane.

10. The method of claim 1 wherein said critical, supercritical or near critical fluid is selected from one or more compounds of the group consisting of nitrous oxide, nitrogen and carbon dioxide.

11. The method of claim 1 wherein said critical, supercritical or near critical fluid has a temperature in the range of approximately 0° C. to 100° C.

12. A method of inactivating one or more virions in a biological fluid comprising:

a) contacting said biological fluid and a supercritical fluid or a critical fluid by introducing said biological fluid into a vessel which contains said supercritical or critical fluid, through a nozzle which releases droplets or a stream of the sample under a nonturbulent condition which has a Reynolds Number less than or equal to 2,000, wherein said contacting is for a sufficient time to inactivate said virion; and b) removing said supercritical or critical fluid from the biological fluid.

* * * * *